(12) United States Patent
Zhang

(10) Patent No.: US 11,656,224 B2
(45) Date of Patent: May 23, 2023

(54) MULTIVALENT GLYCAN MICROARRAY PLATFORM

(71) Applicant: Z Biotech, LLC, Aurora, CO (US)

(72) Inventor: Jian Zhang, Aurora, CO (US)

(73) Assignee: Z BIOTECH LLC, Aurora, CO (US)

( * ) Notice: Subject to any disclaimer, the term of this patent is extended or adjusted under 35 U.S.C. 154(b) by 35 days.

(21) Appl. No.: 17/547,527

(22) Filed: Dec. 10, 2021

(65) Prior Publication Data
US 2022/0099666 A1 Mar. 31, 2022

Related U.S. Application Data

(63) Continuation of application No. 16/099,604, filed as application No. PCT/US2017/031942 on May 10, 2017, now Pat. No. 11,231,415.

(60) Provisional application No. 62/335,341, filed on May 12, 2016.

(51) Int. Cl.
G01N 33/543 (2006.01)
C40B 40/10 (2006.01)
C40B 50/14 (2006.01)
C40B 40/12 (2006.01)
C40B 40/14 (2006.01)

(52) U.S. Cl.
CPC ....... G01N 33/54353 (2013.01); C40B 40/10 (2013.01); C40B 50/14 (2013.01); C40B 40/12 (2013.01); C40B 40/14 (2013.01); G01N 2333/4724 (2013.01)

(58) Field of Classification Search
None
See application file for complete search history.

(56) References Cited

U.S. PATENT DOCUMENTS

| | | |
|---|---|---|
| 8,119,742 B2 | 2/2012 | Dalsin et al. |
| 8,274,075 B2 | 9/2012 | Marks et al. |
| 8,906,832 B2 | 12/2014 | Wong et al. |
| 11,231,415 B2 | 1/2022 | Zhang |
| 2004/0115721 A1 | 6/2004 | Mao et al. |
| 2007/0059769 A1 | 3/2007 | Blixt et al. |
| 2008/0220988 A1 | 9/2008 | Zhou |
| 2010/0113828 A1 | 5/2010 | Daisin et al. |
| 2012/0019915 A1 | 1/2012 | Yan et al. |
| 2012/0231518 A1 | 9/2012 | Cai et al. |
| 2012/0329127 A1 | 12/2012 | Siekmann et al. |
| 2014/0274771 A1 | 9/2014 | Elizazu et al. |
| 2015/0094237 A1 | 4/2015 | Liang et al. |
| 2015/0111764 A1 | 4/2015 | Braunschweig et al. |

FOREIGN PATENT DOCUMENTS

| | | |
|---|---|---|
| CN | 101235098 A | 8/2008 |
| CN | 101338318 A | 1/2009 |
| CN | 102146416 A | 8/2011 |
| CN | 102154349 A | 8/2011 |
| CN | 102154350 A | 8/2011 |
| CN | 102154351 A | 8/2011 |
| CN | 102186878 A | 9/2011 |
| TW | 201425922 | 7/2014 |
| WO | WO 2008/002660 A2 | 1/2008 |

OTHER PUBLICATIONS

Chinese Decision of Rejection dated May 27, 2022 in Chinese Patent Application No. 201780029414.9,—21 pages.
Boozer et al., (2006), "Looking towards label-free biomolecular interaction analysis in a high-throughput formula review of new surface plasmon resonance technologies," Current Opinion in Biotechnology, 17:400-405 DOI 10.1016/j.copbio.2006.06.012.
Campbell et al., (1999) "Electrochemistry Using Single Carbon Nanotube," J. Am. Chem. Soc., 121(15):3779-3780.
Chinese Office Action dated Mar. 1, 2021 in CN 2017800294149.
Chinese Office Action dated Aug. 23, 2021 in CN 2017800294149.
Choi et al., (2010) "Microwave-assisted synthesis of highly water-soluble grapheme towards electrical DNA sensor," Nanoscale, 2:2692-2697 DOI: 10.1039/c0nr00562b.
Kim et al., (2014) "Polyethylenimine-Grafted Polyamidoamine Conjugate for Gene Delivery with High Efficiency and Low Cytotoxicity," Macromolecular Research, 22(7):757-764, DOI 10.1007/s13233-014-2108-8.
Ligang et al., (2009) "Advance in Technology of Gylco-microarray for Glycomics," Biotechnology Bulletin, 6:67-70.
Scobie et al., (2013) "Long-Term IgG Response to Porcine Neu5Gc Antigens without Transmission of PERV in Burn Patients Treated with Porcine Skin Xenografts," The Journal of Immunology, 191:2907-2915, DOI: 10.4049/jimmunol.1301195.
Search Report and Written Opinion, dated Aug. 16, 2017, corresponding to International Application No. PCT/US2017/031942 (filed May 10, 2017).

(Continued)

Primary Examiner — Christopher M Gross
(74) Attorney, Agent, or Firm — Leydig, Voit & Mayer, Ltd.

(57) ABSTRACT

The present invention includes a multivalent glycan microarray for detection of glycan-binding proteins. The multivalent glycan microarray allows a multivalent presentation of glycan on a microarray substrate, which can enhance binding of the glycan binding protein to the glycan microarray. The multivalent microarray includes a solid substrate having one or more branched polymers bonded to it via one or more silane-based linker reagents. The branched polymer in turn is bonded to a glycan, via one or more bifunctional linkers to form the multivalent glycan microarray. Nonspecific binding of glycan binding proteins to the multivalent glycan microarray can be reduced by using a blocking reagent coated on to the microarray substrate, which includes a polyethylene glycol surfactant attached to the solid substrate via a self-crosslinking azido-functionalized silane. Methods for making multivalent glycan microarrays and methods for using same to detect glycan-binding proteins are also disclosed.

20 Claims, 24 Drawing Sheets

(56) References Cited

OTHER PUBLICATIONS

U.S. Appl. No. 16/099,604, filed Nov. 7, 2018.
Chinese Office Action and Search Report dated Jan. 19, 2022 in CN 201780029414.9, 23 pages.

Fig. 4B

B (Blocking Mixture)

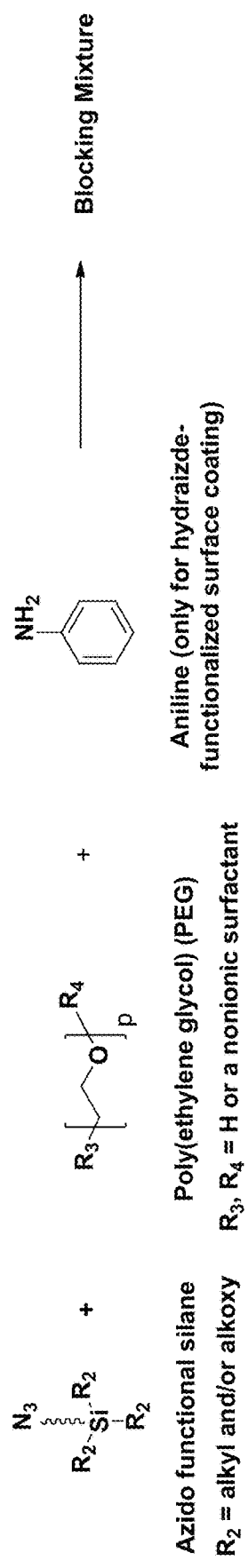

Azido functional silane
$R_2$ = alkyl and/or alkoxy

Poly(ethylene glycol) (PEG)
$R_3$, $R_4$ = H or a nonionic surfactant

Aniline (only for hydraizde-functionalized surface coating)

→ Blocking Mixture

FIG. 4C

C (Coating)

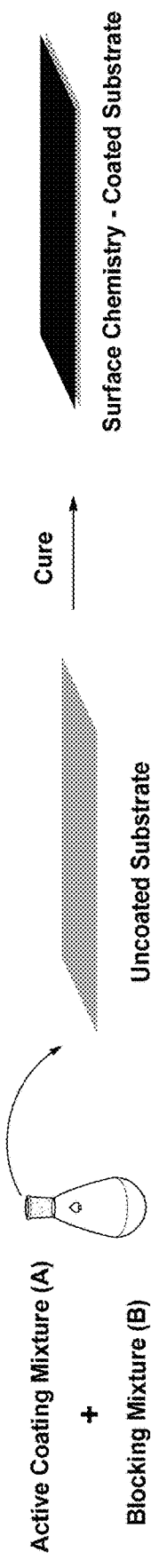

Active Coating Mixture (A)
+
Blocking Mixture (B)

Coating process:
spin-coating,
vapor-coating,
dip-coating,
spray-coating

Uncoated Substrate —Cure→ Surface Chemistry - Coated Substrate

MULTIVALENT GLYCAN MICROARRAY PLATFORM

CROSS-REFERENCE TO RELATED APPLICATIONS

This application is a continuation of U.S. application Ser. No. 16/099,604, filed Nov. 7, 2018, which is a U.S. national phase application of International PCT Application No. PCT/US2017/031942, filed May 10, 2017, which claims priority to U.S. Provisional Application No. 62/335,341, filed May 12, 2016. The disclosures of the aforementioned applications are hereby incorporated by reference in their entireties.

BACKGROUND OF INVENTION

Saccharides (or carbohydrates, or glycans, or sugars) are prominently displayed on the surface of human, plant, and animal cell surfaces. Their structural diversity and abundant presence make saccharides suitable for storing biological signals in forms that are recognizable by other biological molecules, such as families of lectin-like cellular receptors and the anti-glycan antibodies produced by B cells. These binding agents to glycans are called glycan-binding proteins (GBPs). One of the key characteristics of glycan-mediated molecular recognition is multivalent interaction among binding partners. Increasing evidence indicates that not only the structures of glycans but also their multivalent configurations contribute to the selectivity and specificity of glycan recognition and the signaling events mediated by carbohydrate-receptor interactions.

Glycan or saccharide microarrays are small devices capable of presenting a large number of glycan or saccharides molecules on a microarray substrate. They provide a multiplexing means for characterization of protein-glycan interactions. Traditional coated-well binding or immune assays have a number of drawbacks, most notably a labor-intense process due to the singleplex and limited sensitivity. In contrast, microarray-based assays provide multiplexing and superior sensitivity, and are more cost-effective than traditional assays.

Several microarray substrates are available for the immobilization of saccharides or glycans for analysis; however, a significant amount of important biological information cannot be obtained using these platforms due to their low sensitivity and inability to display the saccharides or glycans in a multivalent conformation. There remains a need in the art to further develop glycan microarrays and in particular to develop arrays capable of displaying glycans or saccharides in a multivalent format to increase binding capability for glycan-binding proteins.

SUMMARY OF THE INVENTION

A glycan microarray platform is provided in this invention. It is a ready-to-use platform for multiplexing analysis of glycan interactions with proteins and other biomolecules. In one configuration, it has a functionalized interface for the immobilization of natural or/and synthetic glycans and carbohydrates. The microarray can be in several material forms, including glass or plastic slides with well-organized surface chemistries based on functionalized branched polymers and macromolecules. The branched polymers and macromolecules include but not limited to, polyethylene glycol (PEG), polyethylenimine (PEI), dendrimers, cross-linked polymers, or graft copolymers. The functional groups on the surface chemistries include but not limited to, aldehyde, amine, aminooxyl, avidin (or streptavidin), azide, biotin, carboxylic acids, epoxy, hydrazide, hydrazine, N-hydroxysuccinimide (NHS) and ketone. The branched polymers and macromolecules represent classes of natural or synthetic polymers with structures that are highly branched, which leads to multivalent and high-density probe display when compared to conventional glycan microarray platforms. On this surface, glycans can be covalently or non-covalently attached to each "branch" terminus, which provides improved site density and enables the display of multivalent glycan ligands, with controllable ligand spacing distance. This ability can provide enhanced binding affinity for proteins as the multivalent display of glycans and their ability to cluster to fulfill multivalent interaction requirements and mimic natural glycan display on cell surfaces, and proteins and lipids in the human body. Thus, this multivalent glycan microarray platform can provide a sensitive tool for rapid identification of interactions of proteins and other biomolecules to glycans and carbohydrates.

The protein-glycan (or protein-carbohydrate) interactions are weaker than antibody-antigen interactions (Kd $10^{-3}$-$10^{-6}$ M vs. $10^{-8}$-$10^{-12}$M). Glycan-binding proteins (GBPs) interact weakly with monovalent glycan ligands but strongly with multivalent glycan ligands. The current invention utilizes multivalent binding events between multivalent glycans and glycan-binding proteins. Spherical "tree-like", highly branched polymers can serve as a surface scaffold which can mimic cell surface structures. Furthermore, glycans attached onto the termini of the branched polymers can create multivalent binding events which have high sensitivity because of actual multivalent binding on surface. Functional groups on the array surface are compatible with various glycan structures. Two types of functional groups can be simultaneously anchored at the termini of branched polymers. These functional groups can be used for covalently or non-covalently attaching glycans. The NHS group is used for immobilization of synthetic glycans with an amino tag. The hydrazide group is used for immobilization of natural glycans (free sugars) with free reducing-end. Furthermore, the current invention includes surfaces having both two functional groups, which can attach currently known glycans. The natural glycans have demonstrated greater stabilities than synthetic glycans having amino tags, and are more easily prepared than the synthetic glycans. Synthesis of glycans is usually labor-intensive and time-consuming.

Without wishing to be bound by any particular theory, there may be discussion herein of beliefs or understandings of underlying principles relating to the devices and methods disclosed herein. It is recognized that regardless of the ultimate correctness of any mechanistic explanation or hypothesis, an embodiment of the invention can nonetheless be operative and useful.

BRIEF DESCRIPTION OF THE DRAWINGS

FIG. 4B illustrates an exemplification of blocking reagent to reduce nonspecific binding on to make functionalized substrates.

FIG. 4C illustrates coating functionalized surface chemistries onto a microarray substrate.

DETAILED DESCRIPTION OF THE INVENTION

Figure 1:
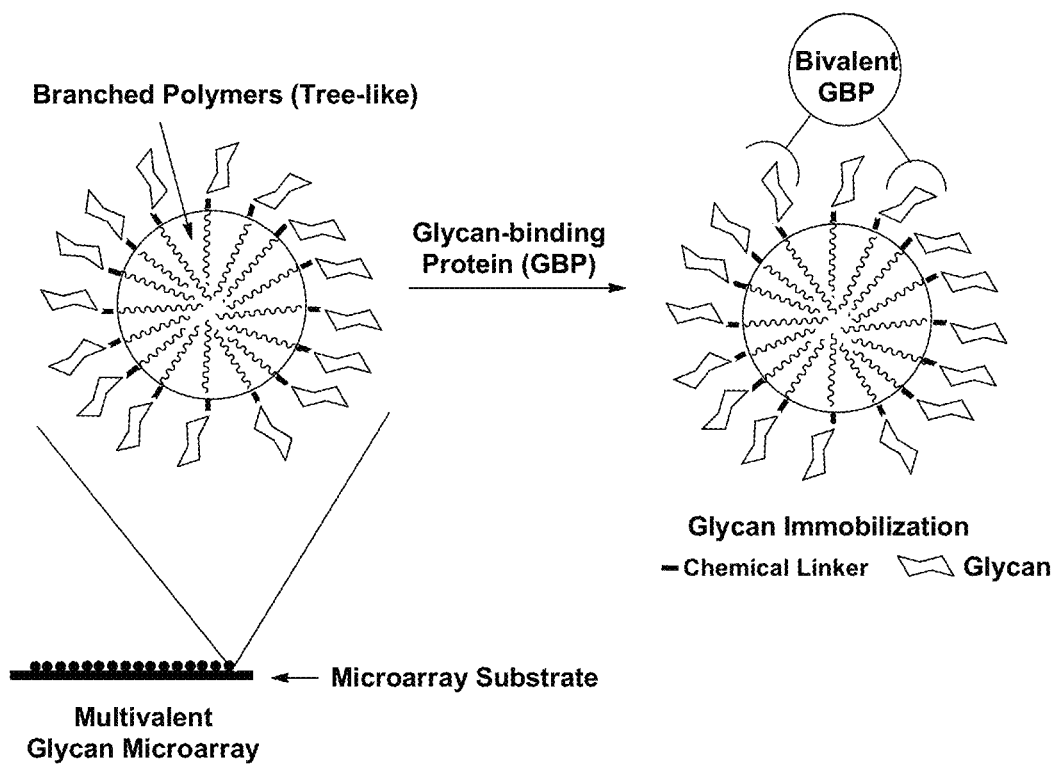
FIG. 1 illustrates the protein-glycan multivalent covalent attachment on a microarray substrate.

In general, the terms and phrases used herein have their art-recognized meaning, which can be found by reference to standard texts, journal references and contexts known to those skilled in the art. The following definitions are provided to clarify their specific use in the context of the invention.

"Glycan" refers to the carbohydrate portion of a glycoconjugates, such as a glycoprotein, glycolipid, or a proteoglycan.

"Multivalent glycan" refers to that glycans are often displayed in multivalent arrangement on proteins or cell surface.

"Multivalent binding event" refers to the interaction of biological molecules with accumulated strength of multiple affinities (or termed functional affinity or avidity). For example, each antibody has at least two antigen-binding sites, therefore antibody-antigen binding is at least bivalent in multivalent binding event.

"Glycan-binding proteins" (GBPs) refers to proteins that recognize and bind to specific glycans and mediate their biological function.

"Biological molecules" refers to any molecule that is present in living organisms, including large molecules such as proteins, carbohydrates, lipids, and nucleic acids, as well as small molecules such as metabolites and natural products.

"Microarray" refers to a technique for collection of microscopic biological molecular spots attached to a solid surface. Scientists can use microarrays to measure binding affinity or expression level of large number of molecules simultaneously. For example, DNA microarrays contains picomole spots of a specific DNA sequence, known as probes. The probes are used to hybridize a DNA or RNA sample (called target) under certain assay conditions. Probe-target hybridization is usually detected and quantified by detection of fluorescence or chemiluminescence-labeled targets to determine relative abundance of nucleic acid sequence in the target.

"Spherical," "branched," or "highly branched" polymer refers to a branching polymer with a branched and/or spherical tree-like shape. Branching occurs by the replacement of a substituent on a monomer subunit by another covalently bonded chain of that polymer, or, in the case of a graft copolymer, by a chain of another type of polymer.

"Crosslinking" or "linking" refers to a chemical bond of one polymer chain to another.

"Crosslinking reagent" or "linking reagent" refers a reagent for binding one polymer chain to another.

Generally speaking, disclosed herein is a microarray substrate surface which is coated with a layer of materials including a spherical, branched or highly branched polymer that can mimic mammalian cells and create a high-density multivalent glycan display on microarray surface. In one embodiment of the invention, there is provided a branched polyamidoamine (PAMAM) dendrimer generation 4 (~5 nm) and contains 64 branches for attaching multiple glycans at each terminus. The branched structure can present glycans in a multivalent format for protein-glycan binding events, which is advantageous because many known glycan-binding proteins have multiple glycan binding sites. Due to the flexibility of the polymer branches, the glycans can be presented to multiple binding sites simultaneously, increasing binding strength of the glycan binding protein to the glycan and thus increasing the sensitivity of detection.

FIG. 1 shows an overview of the structure of the multifunctional glycan microarray platform. Accordingly, in one embodiment of the present invention, a multivalent glycan microarray includes a solid substrate, one or more branched polymers bonded to the solid substrate via one or more non-self-crosslinking silane-based linker reagents; one or more bifunctional linkers, each independently comprising two functional groups, wherein at least one of said functional groups is bonded to said branched polymers; and a plurality of one or more glycans, wherein the plurality of glycans is bonded to said bifunctional linker through the other said functional groups to form the multivalent saccharide or glycan microarray.

The microarray substrate can include transparent and refractive solid-phase material, such as glass (such as silicate glass), ceramic, indium tin oxide (ITO), metal, plastic polymer and silica slides. Plastic polymers include such as polystyrene (Example 8), polypropylene, polycarbonate, polyethylene, high-density polyethylene (HDPE), polyvinyl chloride, polyamide, acrylonitrile butadiene styrene (ABS) and Polyurethane. The substrates include but not limited to, microscope slides, point-of-care diagnostic chips, miniaturized biosensors, micro-reactors and microelectrodes. In one embodiment, the substrate has surface hydroxyl groups which are available for coupling to the organosilane linker reagents disclosed herein.

Prior to use in the present methods, substrates may be prepared or cleaned by processes known in the art, such as a wet-chemistry and/or a plasma cleaning method prior to the coating. In one embodiment, an embodiment of wet-chemistry cleaning includes use of detergents, such as Valtron SP2275 detergent as described below in Example 1.

In one embodiment, the multivalent glycan microarray has one or more branched polymers bonded to the substrate via an organosilane linker reagent. In one embodiment, the organosilane linker reagent includes one or more non-self-crosslinking silane-based linker reagents. A "non self-crosslinking silane-based linker reagent" is a organosilane which carry two different types of reactive groups on the silicon atom, one type of reactive group being an —OR group which are hydrolyzable such as methoxy, ethoxy or acetoxy groups, and a second type of reactive group which is an organo-functional group such as epoxy, amino, methacryloxy, or sulfide, for example. A non-self-crosslinking silane-based linker of the invention, therefore, includes a functionalized alkoxysilane.

The silane-based linker reagent is referred to as "non self-crosslinking" when the organo-functional groups do not react with other silane-based linker reagents to any substantial degree. It is to be noted that the silanol groups are capable of condensing with each other to form polymeric structures, however, under the conditions of the invention, the silanol groups in the non self-crosslinking silane-based linker reagents will primarily condense with hydroxyl groups on the surface of glass, minerals or metals to form stable Si—O—X bonds (X=Si, Al, Fe, etc.)

Examples of functionalized alkoxysilanes include epoxy-functionalized trialkoxysilane, vinyl-functionalized trialkoxysilane, amino-functionalized trialkyoxysilane, methacryloxy-functionalized trialkoxysilane, and isocyanate-functionalized trialkoxysilane. Some specific examples of functionalized alkoxysilanes for use in the present invention include 2-(3,4-epoxycyclohexyl)ethyltriethoxysilane, 2-(3,4-epoxycyclohexyl)ethyltrimethoxysilane, 5,6-epoxyhexyltriethoxysilane, (3-glycidyloxypropyl)triethoxysilane, (3-glycidyloxypropyl)trimethoxysilane, (3-glycidyloxypropyl)methyldiethoxysilane, (3-glycidyloxypropyl)methyldimethoxysilane. Selection of the appropriate functional group on the alkoxysilane is determined by the corresponding terminal group on the branched polymer, as the organo-functional group of the organosilane, under the conditions disclosed in the invention, reacts with a terminal group in the branched polymer.

Selection of the functionalized alkoxysilane will be determined, in part, by the terminal group on the branched polymer (discussed elsewhere herein), as the branched polymer is tethered to the substrate via crosslinking through the functionalized alkoxysilanes.

Figure 2:
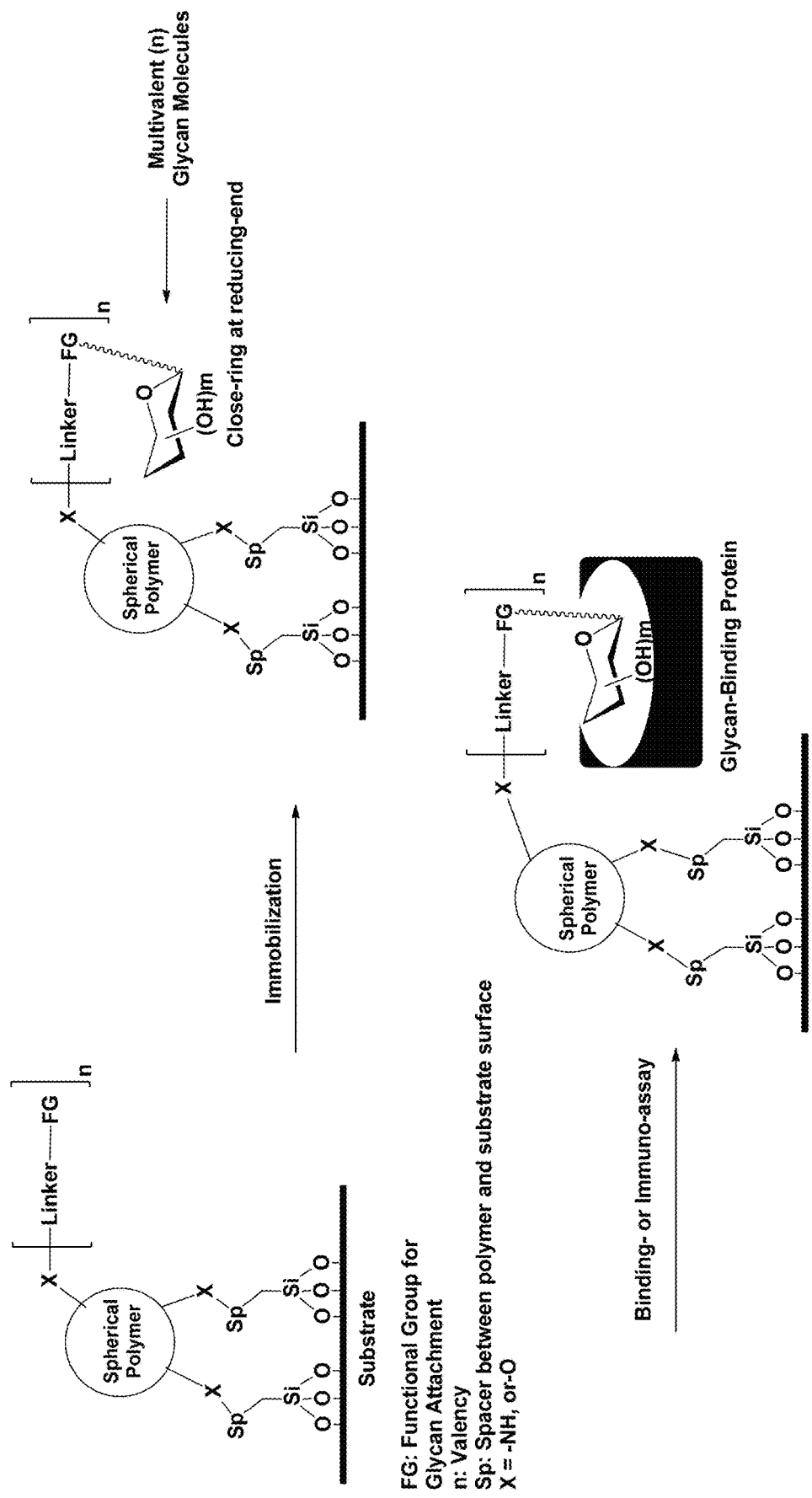
FIG. 2 illustrates a process for immobilization of glycans onto a slide coated with a branched polymer ended with a functional group and subsequent binding- or immune-assays on the glycan microarray.

The multifunctional glycan microarray also includes one or more branched polymers. FIG. 2 shows, in all panels, an exemplification of a branched polymer (or, a spherical branched polymer) with amine or hydroxyl terminal groups on the branched polymer attached to the substrate via the functionalized alkoxysilane. In more detail, the branched polymer has primary amine or hydroxyl terminal groups and can be grafted on an epoxysilane tethering the polymer onto a solid surface having active hydroxyl groups, as shown in FIG. 2. Another branch of the branched polymer has an amine terminal group tethered to a homo- or hetero-bifunctional linker which is then used to tether the branched polymer to attach glycans.

The branched polymer having terminal group(s), in some embodiments, includes a highly branched polymer. Examples of a highly branched polymer includes polyamidoamine (PAMAM) dendrimer, a multi-arm polyethylene glycol (PEG), a highly branched polyethylenimine (PEI) polymer, a PEG-core dendrimer, a multi-arm polyethylene glycol (PEG) polymer, a poly(acrylate), a polyamine, a polyamide, a polyether, a polyester, a poly(methyl acrylate), a polyphenylenes, or a polystyrene. In one embodiment, the branched polymer comprises a polyamidoamine (PAMAM) dendrimer which comprises a number of surface groups (valency sites) in the range from 4, for Generation 0, to 4,096, for Generation 10. In another embodiment, the branched polymer includes a multi-arm polyethylene glycol (PEG) polymer which comprises a number of valency sites in the range from 2, for Y-shaped PEG, to 8, for 8-armed PEG. In another embodiment, the branched polymer includes a highly branched polyethylenimine (PEI) polymer which comprises a number of valency sites in the range 10, for a 800 Da low-molecular-weight PEI, to 211, for a 25,000 Da high-molecular-weight PEI.

Figure 4A:
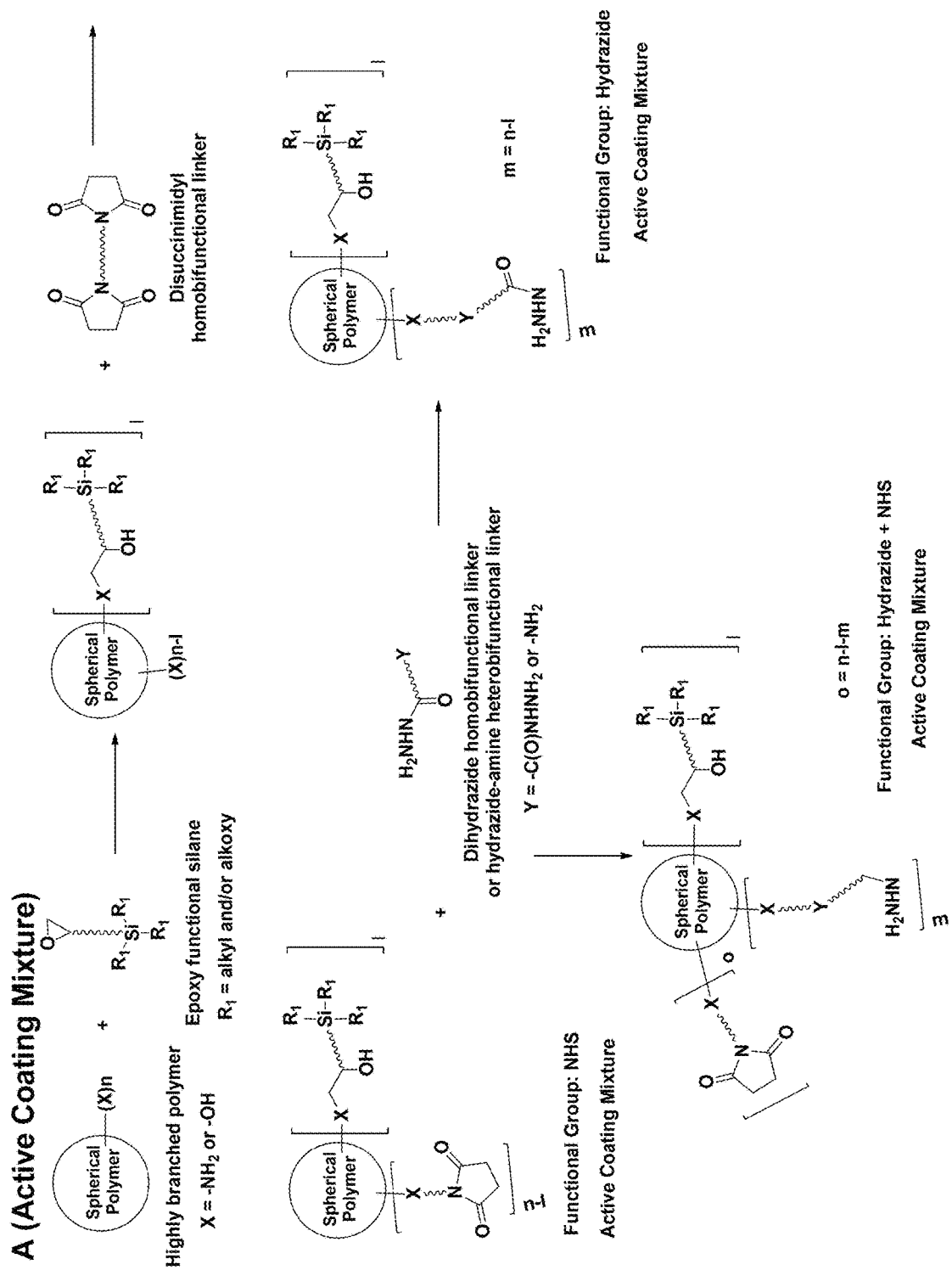
FIG. 4A illustrates an exemplification of coupling chemistries (active coating mixture) for coupling branched polymers to make functionalized substrates.
Figure 4D:
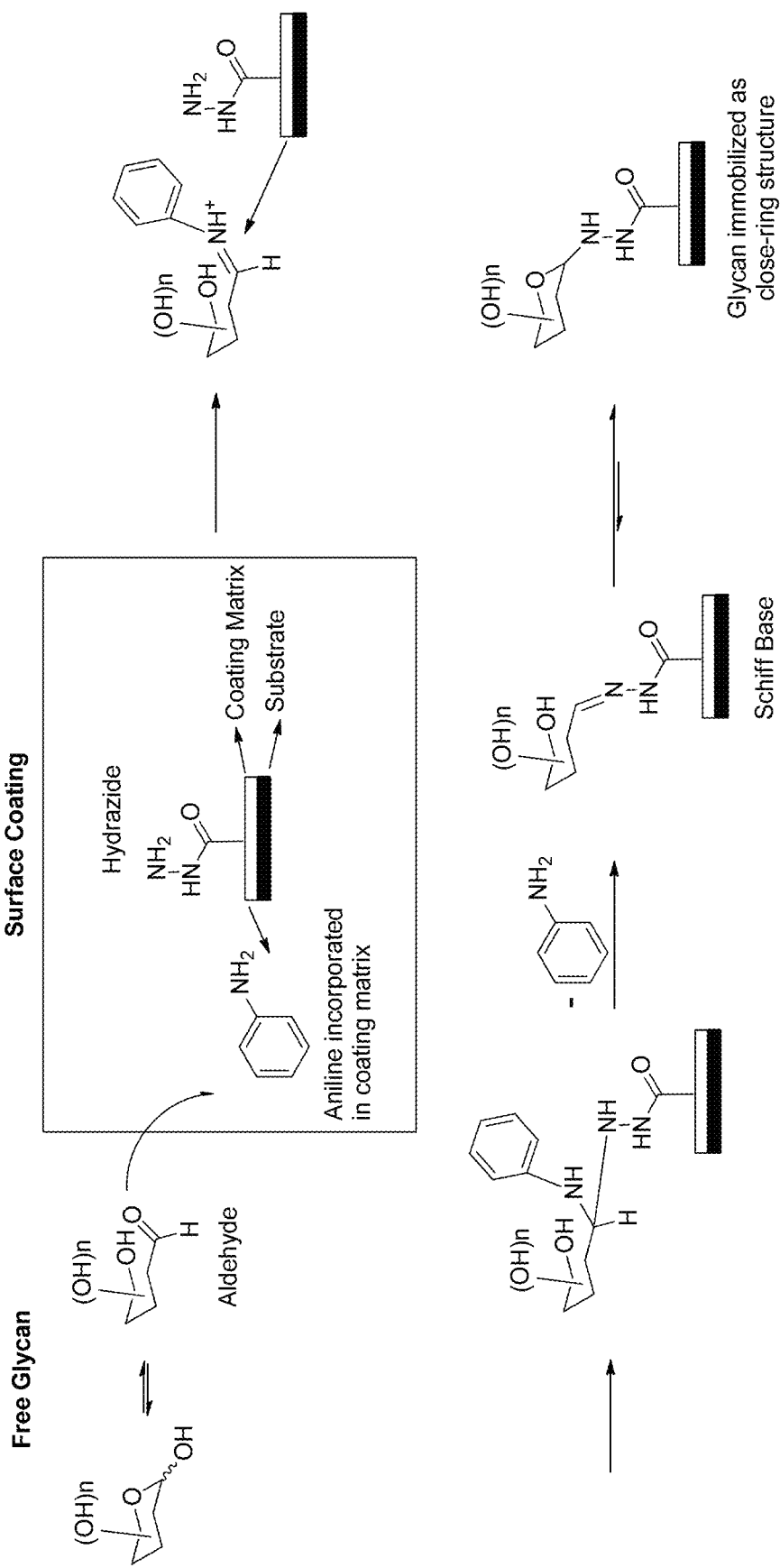
FIG. 4D illustrates the mechanism by which aniline can serve as a catalyst to increase aldehyde-hydrazide coupling efficiency.

The multivalent glycan microarray of the invention also includes a bifunctional linker, which tethers the branched polymer to a glycan through independent functional groups of the bifunctional linker. The invention generally relates attaching glycans (saccharides) to the branched polymer through a linker. FIG. 4A illustrates an exemplification of coupling chemistries for coupling branched polymers to make functionalized substrates. FIG. 4B illustrates an exemplification of blocking reagent to reduce nonspecific binding on to make functionalized substrates. FIG. 4D illustrates the mechanism by which aniline can serve as a catalyst to increase aldehyde-hydrazide coupling efficiency.

The number of bifunctional linkers may be one or more. In some embodiments, there will be a single bifunctional linker between the branched polymer and the glycan. In other embodiments, there may be two or more bifunctional linkers between the branched polymer and the glycan, for example, a branched polymer having one end bonded with one end of a first bifunctional linker with the other end of the first bifunctional linker attached to one end of a second bifunctional linker. The second bifunctional linker may be attached through one functional end to the first bifunctional linker and the other functional end to the glycan. In this manner, there may be three, four or more bifunctional linkers between the branched polymer and the glycan. The number of bifunctional linkers may be chosen, for example, to provide more favorable steric properties, for more efficient linking or to take advantage of commercially available linkers, for example.

The branched polymer(s) may be attached to the glycan through one or more bifunctional linkers that react with a terminal group on another bifunctional linker, or the branched polymer. The branched polymer comprises at least one terminal group which can include a sodium carboxylate terminal group, a primary amine terminal group, a hydroxyl terminal group, an amidoethanol terminal group, a succinamic acid terminal group, a succinamidyl terminal group, and a mixture of primary and secondary amine terminal group. Where the branched polymer includes a terminal amine group, amine-reactive crosslinker groups may be used, which bind to primary amines. Groups that are capable of bonding with primary amines include isothiocyanates, isocyanates, acyl azides, NHS esters, sulfonyl chlorides, aldehydes, glyoxals, epoxides, oxiranes, carbonates, aryl halides, imidoesters, carbodiimides, anhydrides, and fluorophenyl esters. Most of these conjugate to amines by either acylation or alkylation.

Saccharides may generally be attached through, for example, an amine group where the saccharide includes an amine group, or through an aldehyde or ketone where the saccharide includes a reducing sugar. For crosslinking to a saccharide that includes a reducing sugar, a functional moiety reactive with aldehydes or ketones as appropriate will act to crosslink to the saccharide. Aldehyde-reactive crosslinking functional groups include hydrazides to form hydrazone bonds. Aniline can be used to catalyze the hydrazide-aldehyde reaction. Another functional group includes an alkoxyamine group, where the alkoxyamine reacts with the aldehyde to form the stable oxime. Where the saccharide includes an amine group, amine-reactive crosslinker groups may be used, which bind to primary amines, as discussed above.

Thus, the link between the branched polymer and the glycan can occur through crosslinking with a moiety which is a bifunctional linker with a first functional end to attach to said glycan and a second functional end to attach to said branched polymer. In one embodiment, the bifunctional linker includes one or more functional groups which are succinimidyl, hydrazidyl, aminooxyl, aldehyde, amino, azidyl, biotinyl, carboxyl, epoxy, hydrazinyl, N-hydroxysuccinimidyl, and ketonyl functional groups, having a spacer between the functional ends.

In an embodiment, the bifunctional linker includes a first succinimidyl homo-bifunctional linker which can be one or more of N,N'-disuccinimidyl carbonate (DSC), N,N'-disuccinimidyl tartrate (DST), N,N'-disuccinimidyl oxalate (DSO), suberic acid bis(N-hydroxysuccinimide ester), N,N'-disuccinimidyl glutarate (DSG), N,N'-disuccinimidyl suberate (DSS), N,N'-disuccinimidyl homobifunctional poly(ethylene glycol) (PEG) and combinations thereof; and a second hydrazidyl homo-bifunctional linker selected from the group consisting of adipic acid dihydrazide, succinic dihydrazide, oxalyl dihydrazide, 9,10-dihydro-9,10-ethanoanthracene-11,12-dicarboxylic dihydrazide, ethylmalonic acid dihydrazide, isophthalic acid dihydrazide, pimelic acid dihydrazide, carbohydrazide, thiocarbohydrazide, suberic acid dihydrazide, 6-hydrazinonicotinic hydrazide, 4-aminobenzoic hydrazide, 2-amino-isonicotinic acid hydrazide, and combinations thereof.

In an embodiment, the bifunctional linker includes a homo-bifunctional material containing succinimidyl, hydrazide, or aminooxyl functional groups; or a heterobifunctional material containing succinimidyl, hydrazide, or aminooxyl functional groups. In an embodiment, the homo-bifunctional linker comprises N,N'-disuccinimidyl carbonate, adipic acid dihydrazide or any combination thereof.

In another embodiment, there is a first and a second bifunctional linker between the branched polymer and the glycan. In one embodiment, the first bifunctional linker is a disuccinimidyl linker, and the second bifunctional linker is a dihydrazide linker or a hydrazide-amine heterobifunctional linker. In this way a succinimidyl group of the first linker may attach to the second bifunctional linker through the hydrazide group (of the dihydrazide linker) or amine group (of the hydrazide amine linker). From there, the hydrazide functional group of the second linker is available to react with a glycan having a reducing sugar through its aldehyde or ketone groups. Thus, the branched polymer is attached through its amine terminal group to a succinimidyl group of the first linker. The second succinimidyl group of the first linker is then attached alternatively to a glycan through the glycan's amine group, and/or the second succinimidyl group of the first linker is attached through either an amine group or a hydrazide group of the second linker. The second functional group (hydrazide) of the second linker may then be used to attach to the aldehyde or ketone group of a glycan having a reducing end. Other configurations of linkers can be envisioned by one of skill in the art.

In an embodiment, the epoxy-functionalized trialkoxysilane comprises (3-glycidyloxypropyl)trimethoxysilane. In an embodiment, the branched polymer comprises a polyamidoamine (PAMAM) dendrimer, a multi-arm polyethylene glycol (PEG), a highly branched polyethylenimine (PEI) polymer, or any combination thereof.

A glycan suitable for use in the present invention can be determined by one of skill in the art. The glycan can be a natural or artificial glycan and determining which glycan(s) to use will depend on, for example, the particular glycan-binding protein that one wishes to detect, i.e., the glycan array can include a glycan which is a known binding partner or ligand for the glycan-binding protein. The glycans printed on glycan arrays include but not limited to natural glycans (free sugars each containing a free reducing-end) and synthetic glycans, each optionally containing an amino tag. In general, natural glycans are more stable and easier to obtain than the synthetic glycans. A natural glycan can be specifically immobilized onto a hydrazide-functionalized multivalent substrate (see Example 6). A synthetic glycan containing an amino tag can be specifically immobilized onto a NHS-functionalized multivalent substrate (see Examples 7 and 8).

Accordingly, the glycan(s) in the multivalent glycan microarray can be, for example, a monosaccharide, an oligosaccharide or a polysaccharide. The applicant has carried out tests with numerous glycans to show that any glycan which is a useful ligand for a glycan-binding partner, taking into account steric and other considerations for an assay format, can be used in the invention. In particular, useful ligands include high-mannose N-glycans, complex N-glycans, hybrid N-glycans, O-GalNAc O-glycans, O-mannose O-glycans, O-GlcNAc O-glycans, blood groups and lewis antigen glycans, human milk oligosaccharides, glycosphingolipid glycans, glycosaminoglycans, bacterial glycans, and glycan-containing natural products. Examples of glycans which can be used in the present invention include any of the glycans disclosed herein.

In an embodiment, the adjacent multivalent glycan probes are separated by a separation distance that is greater than or equal to 20 μm and less than or equal to 500 μm. In an embodiment, a plurality of multivalent glycan probes covalently or non-covalently attached to said functional groups; wherein different probes are provided in different regions, in a multiplex format.

The multivalent glycan microarray, as described herein, allows for binding interactions between glycan(s) tethered to the array and target glycan-binding proteins. Any moiety that is capable of binding to glycans may be detected and/or quantified using the methods and microarrays of the invention. In particular, glycan-binding proteins such as a lectin, a lectin-like cellular receptor, an antibody, fused proteins, native proteins, recombinant proteins, or any combination thereof may be detected. An exemplary glycan-binding protein is an antibody which detects carbohydrate epitopes. Such an antibody may be an IgA antibody, IgD antibody, IgE antibody, IgM antibody or an IgG antibody.

Figure 11A:
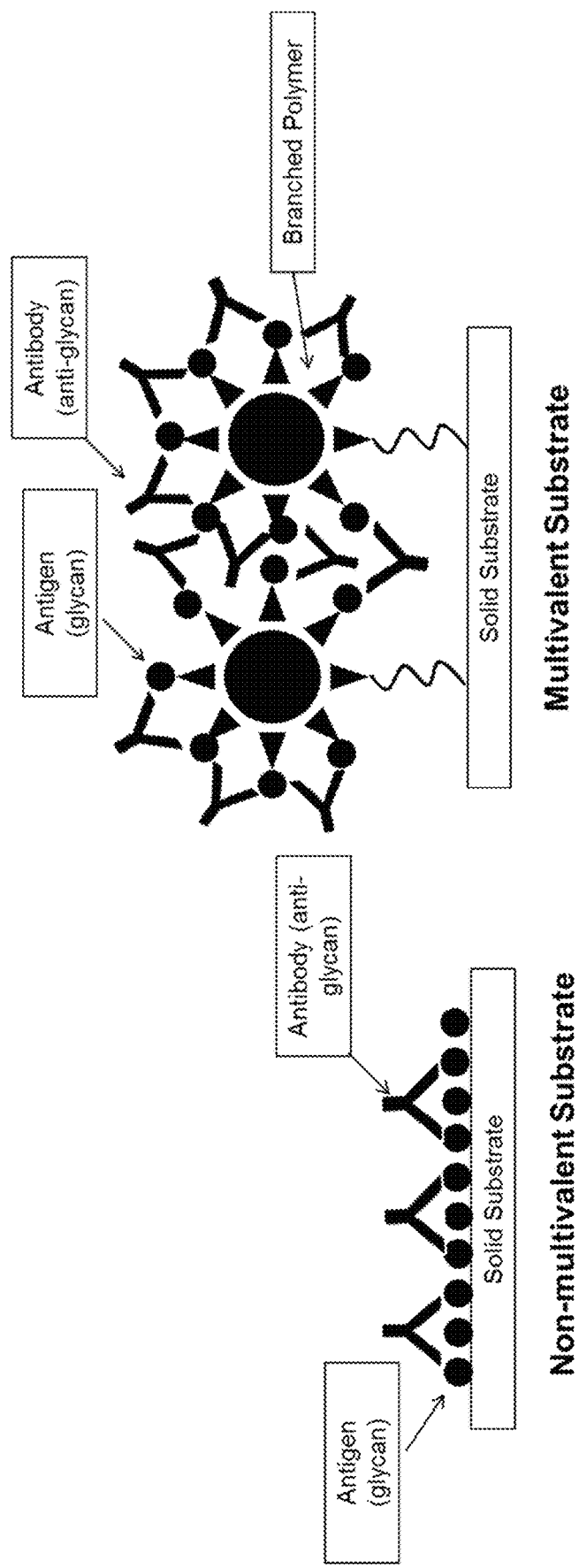
FIG. 11A illustrates an envisioning of an antibody-antigen (glycan) binding event on the multivalent substrate of the present invention (right) and non-multivalent substrates of the prior art (left).
Figure 11B:
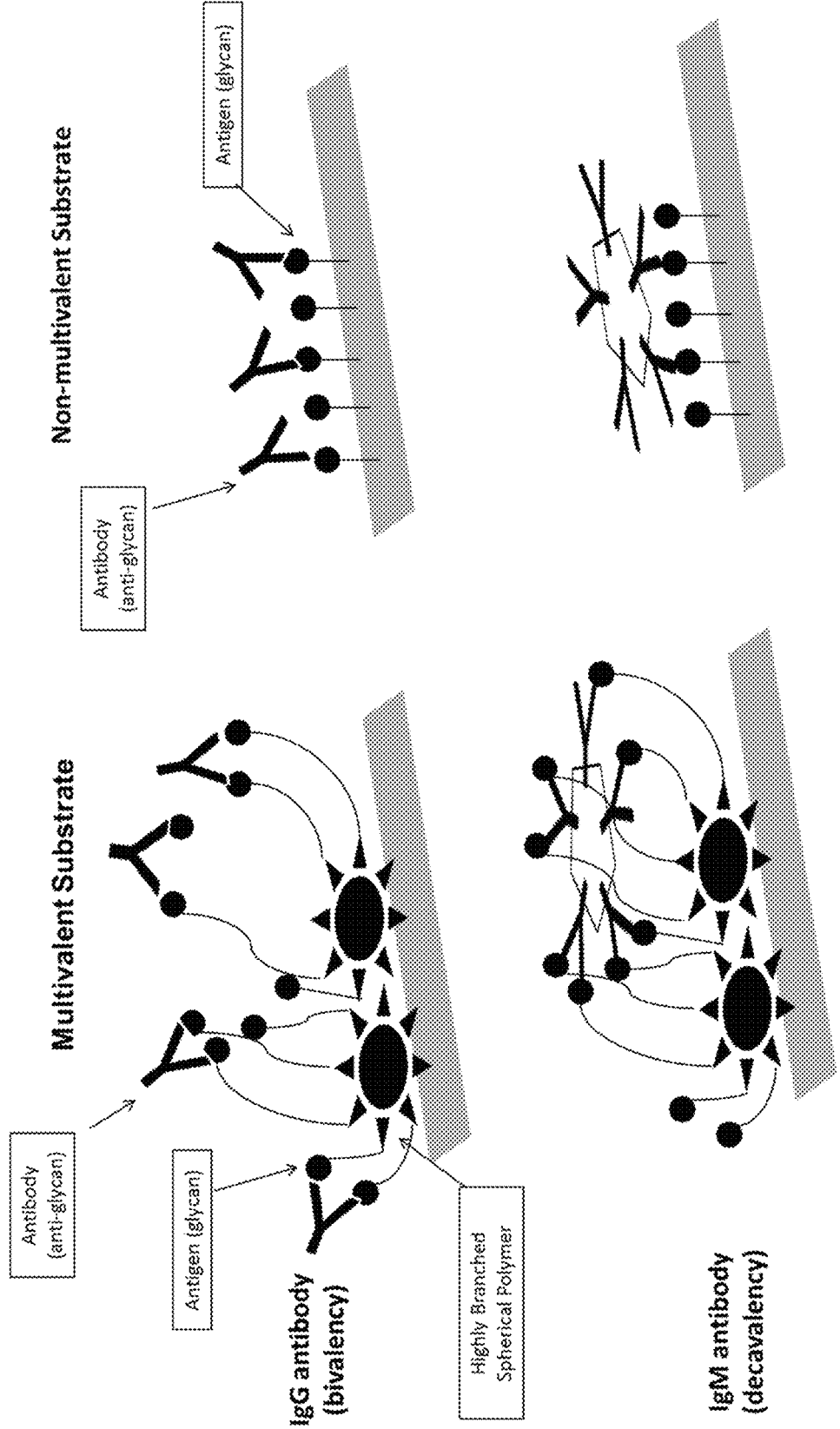
FIG. 11B illustrates an envisioning of an antibody-antigen (glycan) binding event a multivalent glycan substrate of the invention for IgG (bivalent) or for IgM (decavalent).

The particular advantage to use of this system to detect antibodies includes the fact that antibodies are multivalent. Thus, for highest binding affinity, antibodies require a multivalent binding environment to accumulate strength of multiple affinity (also termed avidity). For example, IgG antibodies are bivalent and IgM antibodies are decavalent. Without being bound by theory, the Applicant believes that on the microarray substrate surface, antigens displayed in multivalent format can bind to more than one antibody molecule and form stable antigen-antibody interaction, thus lead to high binding avidity (FIG. 11A and FIG. 11B.) Through the branched polymer structure in surface coating, the multivalent glycan microarray substrate of the invention can create multivalent binding events for antibody-glycan (antigen) interaction.

Useful antibodies to detect include anti-STn antibodies (B72.3, STn 219, CC49), anti-Neu5Gc antibody, CD15 (SSEA-1) antibody (anti-Lewis X antibody), CD15s antibody (anti-sialyl lewis X antibody), anti-Tn antibody (Tn 218), anti-MUC1 antibody, 2G12 antibody, PGT121, PGT128 antibody, HIV broadly neutralizing antibodies, anti-Gb3 antibody (CD77 antibody), anti-fucosyl-GM1 antibody (BMS-986012), anti-GM3 antibody, anti-Lewis A antibody, anti-sialyl lewis A antibody, anti-Globo-H antibody. Other antibodies to detect include anti-GD2 antibody (e.g., Dinutuximab), and anti-NGcGM3 antibody (e.g., 14F7 mAb, Racotumomab).

In an embodiment, where the glycan-binding protein to detect is an antibody, binding of the antibody may be detected and/or quantitated through methods known in the art, such as detection with a tagged secondary antibody. In an embodiment, the secondary antibodies comprise anti-human IgG, anti-human IgM, or anti-human IgA isotypes.

In one aspect of the multifunctional glycan microarrays of the invention, the microarray further comprises additional component(s) which act to reduce the background of the assay during operation. Such component(s) may be called blocking reagents or reagent, for example. Components to reduce background include those known in the art. In an embodiment, the blocking reagents or reagent include an azide-functionalized trialkoxysilane crosslinking reagent for stabilizing the surface coating layer and also includes a PEG such as poly(ethylene glycol) sorbitol hexaoleate for reducing background signal and reducing non-specific binding.

In one embodiment of the instant invention, the blocking reagent includes a poly(ethylene glycol) (PEG) or a PEG nonionic surfactant, which may be optionally attached to the solid surface through one or more self-crosslinking silane-based linker reagents. Exemplifications of a PEG or PEG nonionic surfactant include a PEG polymer, poly(ethylene glycol) sorbitol hexaoleate, poly(ethylene glycol) sorbitan tetraoleate, and combinations thereof.

A "self-crosslinking" silane-based crosslinker has a different functionality, in some regards, than a "non self-crosslinking silane-based linker reagent." Both types are organosilane which carry two different types of reactive groups on the silicon atom. In both instances one of the two types of reactive group are an —OR group which are hydrolysable such as methoxy, ethoxy or acetoxy groups, and a second type of reactive group which is an organo-functional group which is capable of self-crosslinking. The silane-based linker reagent is referred to as "self-crosslinking" when the organo-functional groups do react with other silane-based linker reagents to a substantial degree through the organo-functional groups. Exemplifications of self-crosslinking silane-based linker reagent include an azido functionalized trialkoxysilane which includes azido functionalized trialkoxysilanes 3-azidopropyltriethoxysilane, p-azidomethylphenyltrimethoxysilane, 6-azidosulfonylhexyltriethoxysilane, 4-(azidosulfonyl)phenethyltrimethoxysilane, (azidomethyl)phenethyltrimethoxysilane, or combinations thereof.

In an embodiment, the multivalent glycan microarray may further comprise a label agent, wherein said label agent is configured to bind to an immobilized or bound glycan-binding protein to produce a detectable signal indicative of a binding between said at least one glycan and said target glycan-binding protein.

Surface Coating Process

In one embodiment, a method for making a functionalized substrate for a multivalent glycan microarray includes providing a substrate having a contact surface as described herein. An active coating mixture is provided (in some embodiments, called Solution A). The active coating mixture can include one or more non self-crosslinking silane based linker reagents, as well as one or more branched polymers, and one or more bifunctional linkers. After a functionalized surface is created, the method also includes curing said functionalized substrate, wherein said functionalized substrate comprises a plurality of functional groups for binding glycans to form said multivalent glycan microarray. The method, in embodiments, further includes contacting the functionalized substrate with at least one glycan under conditions to allow bonding of said glycan to said functional groups to form a multivalent glycan microarray.

In one embodiment, the method further includes contacting at least a portion of the contact surface of the solid substrate with a blocking mixture (in some embodiments, called Solution B) to reduce nonspecific binding of glycan-binding proteins to the solid substrate. The blocking mixture comprises a self-crosslinking silane-based linker reagent, and a blocking reagent comprising poly(ethylene glycol) (PEG) or a PEG nonionic surfactant.

In an embodiment, contacting comprises spin-coating, vapor-coating, dip-coating, spray-coating, or any combination thereof. In an embodiment, the spin-coating is used to apply a small volume of coating solution onto said contact surface, said small volume is between 0.1 μl/mm$^2$ and 5 μl/mm$^2$. In an embodiment, the spinning rate utilized in said spin-coating is between 3,000 revolutions per minute (rpm) and 5,000 rpm. In an embodiment, the spin-coating is performed in more than one spin-coating step. In an embodiment, the first said spin-coating is performed at a first spinning rate of 500 revolutions per minute (rpm) for a duration of 10 seconds, wherein a first rate of acceleration of the spinning is of 100 rpm per second until said first spinning rate is achieved; and wherein a second said spin-coating is performed at a second spinning rate of 4,000 rpm for a duration of about 30 seconds, wherein a second rate of acceleration of 300 rpm per second until said second spinning rate is achieved. In an embodiment, the total duration of said first spin-coating and second spin-coating steps is between 30 seconds and 90 seconds.

In an embodiment, the curing step comprises a thermal curing process in a vacuum oven or an ultraviolet (UV) curing process in a UV crosslinker. In an embodiment, the thermal curing process comprises a curing temperature, a curing duration, and a curing pressure. In an embodiment, the curing temperature is between 70° C. and 150° C.; wherein said curing duration is between 1 and 4 hours, and wherein said curing pressure is less than atmospheric pressure.

Figure 3:
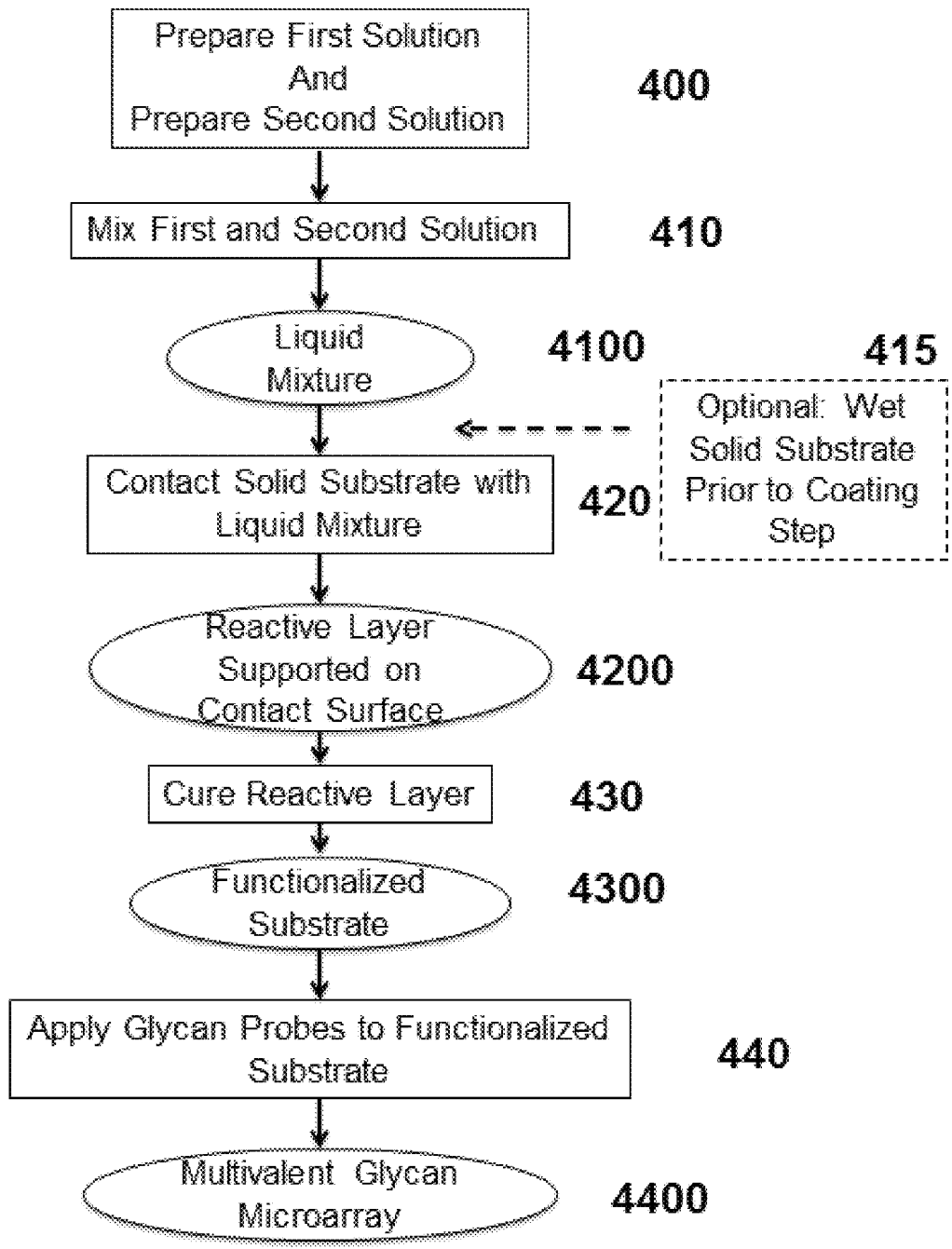
FIG. 3 provides a schematic illustration of a method for making a multivalent glycan microarray.

FIG. 3 provides a schematic illustration of a method for making an embodiment of a multivalent glycan microarray. Two solutions (Solution A: active coating mixture; Solution B: blocking mixture) are prepared 400, and then mixed together 410 to form the final coating solution 4100. A first solution, Solution A, is an active component for forming a multivalent structure on surface. A more detailed chemical reaction in the preparation of Solution A is provided in FIG. 4A. A second solution, Solution B, includes two components, a cross-linker and a PEGylated polymer. A more detailed chemical reaction in the preparation of Solution B is provided in FIG. 4B. In the second solution, the cross-linking reagent is used for stabilizing surface coating and enhancing coating shelf-life. A PEGylated polymer material is used for achieving a substrate with low background and low non-specific binding.

A step-by-step chemical reaction strategy is used for forming the active component in Solution A. More specifically as shown in FIG. 4A, the branched polymer with branched amine or hydroxyl termini are reacted with an epoxy functional silane (such as 3-glycidyloxypropyl) trimethoxysilane) indicated in FIG. 4A. The polymer-silane conjugate can react with a disuccinimidyl homobifunctional linker (such as N,N'-disuccinimidyl carbonate) as shown in the FIG. 4A. The disuccinimidyl homobifunctional linker contains two N-hydroxysuccinimide (NHS) functional groups. Therefore, a NHS-functionalized branched polymer is formed. Furthermore, as shown in FIG. 4A, another dihydrazide homobifunctional linker or hydrazide-amine heterobifunctional linker can be reacted with the NHS groups to form hydrazide functional groups. Through adjusting the molar ratio of the reaction reagent, a bifunctional coating solution containing both NHS and hydrazide functional groups is formed for coating a substrate used for immobilization of both synthetic and natural glycans (FIG. 4A).

In solution A, for example, the epoxy functional silane may be present at an amount of between 5 and 25 mM, between 5-20 mM, or about 10 mM. The branched polymer may be in an amount of between about 0.5-5 mM, or between about 1 mM and about 5 mM, or about 2.5 mM. The bifunctional linker may be present in an amount of between about 20 mM to about 100 mM, between about 20 mM and about 50 mM, or about 40 mM. Where a second bifunctional linker is present the second bifunctional linker may be added in an amount of about 20 mM to about 100 mM, or between about 40 mM and about 90 mM, or about 80 mM. The ratios of each component for a particular application and for a particular reaction mixture may be determined by one of skill in the art.

In solution B, for example, can include two components, a cross-linker and a PEGylated polymer. The crosslinker, a self-crosslinking silane, may be present in amounts of between about 1 and 10 mM, or about 8 mM, and the PEGylated polymer may be present in amounts of between about 0.5 and 10 mM, or about 4.5 mM. The ratios of each component for a particular application and for a particular reaction mixture may be determined by one of skill in the art.

The liquid mixture 4100 of the first and second solutions is applied to a substrate using a coating method 420, to produce a reactive layer supported on the contact surface 4200. The coating methods comprise spin-coating, vapor-coating, dip-coating and spray-coating. Preferably spin-coating is used to apply a small volume of coating solution onto the substrate surface. As shown in FIG. 4C, the coating mixture is applied onto the substrate. Optionally, the substrate can be treated by a wetting step 415. The wetting time is based on roughness of the substrate surface. More preferably, the substrates are wetted for 1 minute prior to being spun. Spinning rate is set at 3,000-5,000 rpm. More preferably, the substrates are spun at two phase of speed. For example, as described in Example 1, the substrates is spun on the spin-coater using a two-step coating program (step 1: spin at 500 rpm for 10 seconds with acceleration of 100 rpm/s; step 2: spin at 4,000 rpm for 30 seconds with acceleration of 300 rpm/s). Spinning time is 30-90 seconds.

After the coating mixture is applied onto substrate surface 420, a thermal curing process or UV curing process 430 is applied to adhere the reactive layer 4200 onto substrate surface and form crosslinking structure on substrate surface to form a functionalized substrate 4300. In a thermal curing process, the curing temperature and time is dependent on the tolerance temperature and property of the substrate material. More preferably, the temperature is set at 100° C. for glass substrate and 70° C. for plastic substrates; and the curing time is 1~4 hours.

Fabrication of Glycan Array on Multivalent Microarray Substrates

Wetting

Glycan probes can be spotted onto the multivalent substrates 440 using a microarray printing equipment to form the multivalent glycan microarray 4400. The microarray printing equipment is a micro-dispensing system that can deliver picoliter to microliter amount of liquid onto microarray substrates. It includes but not limited to contact and non-contact printing equipment. Print Buffer used for dissolving glycan probes are buffers containing additives for enhancing spotting quality. The pH value for the Print Buffer is 5-9. The additives could be a non-ionic or ionic detergent that can enhance spot uniformity and alignment on array and/or a polyol reagent such as glycerol or trehalose to prevent spot solution evaporation and enhance spot morphology. More preferably as described in Example 6, the Print Buffer contains 0.15 M sodium phosphate, 0.1% Glycerol, 0.01% SDS (pH 5.8) is suitable for spotting natural glycans onto the hydrazide-functionalized multivalent substrates.

After printing, immobilization of the glycan arrays can be enhanced by a treatment, such as thermal heat at 50° C. and long-time incubation in high relative humidity. More preferably as described in Example 6, the microwave treatment for 10 minutes is an effective and time-saving method for glycan immobilization.

In an aspect, a method for making a multivalent glycan microarray, comprises: providing a solid substrate having a contact surface, contacting at least a portion of said contact surface of said solid substrate with a liquid mixture comprising a plurality of coating reagents to form a reactive layer supported by said contact surface; wherein said coating reagents comprise a first solution and a second solution; wherein said first solution comprises: a non self-crosslinking epoxy-functionalized silane; a branched polymer; and a bifunctional linker; wherein said second solution comprises: a self-crosslinking (e.g., azide)-functionalized silane; a blocking reagent comprising either a poly(ethylene glycol) (PEG) or a PEG nonionic surfactant (e.g., poly(ethylene glycol) sorbitol hexaoleate); and a solvent; curing said reactive layer, thereby forming a functionalized substrate comprising a plurality of said functional groups for immobilizing glycans onto said microarray substrate; applying glycan probes to said plurality of said functional groups, wherein said multivalent glycan probes covalently or noncovalently attach to said functional groups; wherein different glycan probes are provided in different locations on said functionalized substrate to generate said multivalent glycan microarray.

Additionally, addition of aniline into the reaction, particularly, in the second solution can enhance immobilization capability for the hydrazide functional group, which is used for immobilization of glycan having free reducing-end or aldehyde group(s). As shown in the Examples, glycan arrays using aniline showed significant enhancement in sensitivity for detection of lectins and anti-glycan antibodies.

The present invention also includes a method for identification of interactions between a multivalent glycan microarray and a glycan-binding protein. The method includes providing a sample which contains, or is thought to contain, at least one glycan-binding protein which is a binding partner with at least one glycan in the multivalent glycan microarray and providing a multivalent glycan microarray; contacting the sample and the multivalent glycan microarray under conditions which allow binding between the glycan binding protein and a glycan on the microarray, and detecting an interaction between the glycans in the multivalent glycan microarray and said glycan-binding protein.

In an aspect, a method for identification of interactions between multivalent glycan-binding epitopes and glycan-binding proteins, comprises: providing a plurality of glycan-binding proteins; providing a multivalent glycan microarray having multivalent glycan-binding epitope functional groups tethered to a solid substrate, wherein said target glycan-binding protein is bound to said multivalent glycan-binding epitopes; and providing at least one label agent; wherein said label agent is configured to bind to said target glycan-binding protein to produce a detectable signal indicative of binding between said at least one multivalent glycan-binding epitope and said target glycan-binding protein; wherein said multivalent glycan microarray is exposed to said plurality of glycan-binding proteins; detecting an interaction between said multivalent glycan-binding epitope and said target glycan-binding protein; and quantifying a strength of said detected interaction, thereby identifying the interaction between a glycan-binding protein and said multivalent glycan-binding epitopes. In an embodiment, the method further comprises: displaying said strength of detected interaction.

In one embodiment, after immobilization of the glycan onto the functionalized surface, the multivalent glycan microarray can optionally be treated with a blocking buffer as known in the art to further reduce nonspecific binding of the glycan-binding protein. It is noted that blocking reagents as described herein, incorporated into the surface coating, will function to reduce nonspecific binding, which a blocking buffer may further reduce nonspecific binding. One such blocking buffer includes a protein-containing buffer with a pH 7-9, such as 1% BSA in PBST (pH 7.4) in Example 6 or 25 mM ethanolamine in 100 mM boric acid, 0.01% Tween 20 (pH 8.5) in Example 7. The protein-glycan binding can be detected and quantified by a reader such as a fluorescence-based microarray scanner.

In an embodiment, the detecting is accomplished by generating said signal from fluorescence, chemiluminescence, biochemiluminescence, surface plasmon resonance, colorimetry, radioisotope, molecular reporter, electrochemiluminescence, or any combination of techniques. In an embodiment, the target glycan-binding proteins are labeled with an affinity tag, a solubilization tag, a chromatography tag, a short peptide epitope tag, a fluorescence tag, or a combination thereof for detection. In an embodiment, the affinity tag comprises biotin, chitin binding protein (CBP), maltose binding protein (MBP), poly(His) tag and glutathione-S-transferase (GST); wherein said solubilization tag comprises thioredoxin (TRX) and poly(NANP); wherein said chromatography tag comprises FLAG-tag; wherein said short peptide epitope tag comprises V5-tag, Myc-tag, and HA-tag; and wherein said fluorescence tag comprises green fluorescent protein (GFP). In an embodiment, the glycan-binding proteins are free of any labels. In an embodiment, the glycan-binding proteins are detected by surface plasmon resonance.

For protein-glycan interaction events, the present inventors found that multivalent slides exhibit greater binding affinity than any microarray substrate on market, especially for antibody-glycan interaction. As shown in FIG. 12A-D, detection of anti-glycan antibodies (2G12, anti-CD15 and anti-CD15s) on NEXTERION Slide H microarray substrate and the multivalent glycan microarray substrate was compared. The multivalent glycan microarray substrates showed much higher binding affinity and broader binding profile than the NEXTERION Slide H microarray substrate.

In an embodiment, a composition or compound of the invention is isolated or purified. In an embodiment, an isolated or purified compound is at least partially isolated or purified as would be understood in the art. In an embodiment, the composition or compound of the invention has a chemical purity of at least 95%, optionally for some applications at least 99%, optionally for some applications at least 99.9%, optionally for some applications at least 99.99%, and optionally for some applications at least 99.999% pure.

As used herein, the term "polymer" refers to a molecule composed of repeating structural units connected by covalent chemical bonds often characterized by a substantial number of repeating units (e.g., equal to or greater than 3 repeating units, optionally, in some embodiments equal to or greater than 10 repeating units, in some embodiments greater or equal to 30 repeating units) and a high molecular weight (e.g. greater than or equal to 10,000 Da, in some embodiments greater than or equal to 50,000 Da or greater than or equal to 100,000 Da). Polymers are commonly the polymerization product of one or more monomer precursors. The term polymer includes homopolymers, or polymers consisting essentially of a single repeating monomer subunit. The term polymer also includes copolymers which are formed when two or more different types of monomers are linked in the same polymer. Copolymers may comprise two or more monomer subunits, and include random, block, brush, brush block, alternating, segmented, grafted, tapered and other architectures. Useful polymers include organic polymers or inorganic polymers that may be in amorphous, semi-amorphous, crystalline or semi-crystalline states. Cross linked polymers having linked monomer chains are useful for some applications.

An "oligomer" refers to a molecule composed of repeating structural units connected by covalent chemical bonds often characterized by a number of repeating units less than that of a polymer (e.g., equal to or less than 3 repeating units) and a lower molecular weights (e.g. less than or equal to 1,000 Da) than polymers. Oligomers may be the polymerization product of one or more monomer precursors.

EXAMPLES

Example 1: Preparation of a Polyamidoamine (PAMAM) Dendrimer Generation 2 Coating Functionalized with N-Hydroxysuccinimide (NHS) Groups on Glass Slides Microscope slides are cleaned with 2% Valtron SP2275 detergent in sonication bath heated to 60° C. Then they are dried in a vacuum oven at 100° C. for 30 minutes. A coating Solution A, the first solution, or "active coating mixture," is prepared by mixing 10 mM (3-Glycidyloxypropyl) trimethoxysilane (GOPS) and 2.5 mM PAMAM dendrimer generation 2 in DMSO. Amounts of 5, 10 and 20 mM GOPS were tested and 10 mM selected; amounts of 0.5 mM, 1 mM, 1.5 mM, 2 mM, 2.5 mM, 3 mM, 3.5 mM, 4 mM, 4.5 mM, and 5 mM were tested and 2.5 mM selected. All amounts tested were successful. The mixture is stirred for 30 minutes. In a separate vial, 40 mM N,N'-disuccinimidyl carbonate is dissolved in DMSO and the solution is added dropwise to the mixture containing GOPS and dendrimer (form Solution A). Amounts of 40 mM and 80 mM N,N'-disuccinimidyl carbonate were tested and 40 mM selected. All amounts tested were successful. The first solution, Solution A, is stirred for additional 30 minutes. A coating Solution B, the second solution, or the "blocking mixture" is prepared by mixing 4.52 mM poly(ethylene glycol) sorbitol hexaoleate (2.26, 4.52, and 9.04 mM were tested successfully) and 8.26 mM 6-azidosulfonylhexyltriethoxy silane (2.07, 4.13 and 8.26 mM were tested successfully) in DMSO. The second solution, Solution B, mixture is stirred for 30 minutes. The Solution A and the Solution B are mixed in a 1 to 6 volume ratio. The mixture is stirred for 10 minutes and then diluted 1.2 times with DMSO. The final coating solution is filtered through a 0.2 µM DMSO-safe filter and dispenses 1 mL onto each microscope slide covering whole surface area. After allowing the coating solution wetting for 1 minute, the microscope slide is spun on the spin-coater using a two-step coating program (step 1: spin at 500 rpm for 10 seconds with acceleration of 100 rpm/s; step 2: spin at 4,000 rpm for 30 seconds with acceleration of 300 rpm/s). The coated slides are maintained in the vacuum oven (200 mm Hg) at room temperature for 20 minutes. The oven is then heated to 100° C. and the coating is cured for 2 hours under this condition. The heat of the oven is turned off and the slides are allowed to cool down to 50° C. in argon. Then the slides are cooled down to room temperature in ambient air. The slides are rinsed with MilliQ water twice in sonication bath, 2 minutes each time. Then the slides are dried in an IR heater for 15 minutes and then dried in the vacuum oven at 50° C. for 15 minutes.

Example 2: Preparation of a Polyamidoamine (PAMAM) Dendrimer Generation 2 Coating Functionalized with Hydrazide Groups on Glass Slides Microscope slides are cleaned with 2% Valtron SP2275 detergent in sonication bath heated to 60° C. Then they are dried in a vacuum oven at 100° C. for 30 minutes. A coating Solution A, the first solution, or active coating mixture, is prepared by mixing 10 mM (3-Glycidyloxypropyl) trimethoxysilane (GOPS) and 2.5 mM PAMAM dendrimer generation 2 in DMSO. The mixture is stirred for 30 minutes. In a separate vial, 40 mM N,N'-disuccinimidyl carbonate is dissolved in DMSO and the solution is added dropwise to the mixture containing GOPS and dendrimer. The mixture is stirred for additional 30 minutes. Then 80 mM adipic acid dihydrazide (48, 56, 64, 72 and 80 mM were tested successfully) is added to the mixture and stirred for additional 30 minutes (form Solution A). A coating Solution B, the second solution, or the blocking mixture, is prepared by mixing 4.52 mM poly(ethylene glycol) sorbitol hexaoleate and 8.26 mM 6-azidosulfonylhexyltriethoxy silane in DMSO. The second solution, Solution B, mixture is stirred for 30 minutes. The first solution, Solution A, and the second solution, Solution B, are mixed in a 1 to 6 volume ratio. The mixture is stirred for 10 minutes and then diluted 1.2 times with DMSO. The final coating solution is filtered through a 0.2 µM DMSO-safe filter and dispenses 1 mL onto each microscope slide covering whole surface area. After allowing the coating solution wetting for 1 minute, the microscope slide is spun on the spin-coater using a two-step coating program (step 1: spin at 500 rpm for 10 seconds with acceleration of 100 rpm/s; step 2: spin at 4,000 rpm for 30 seconds with acceleration of 300 rpm/s). The coated slides are maintained in the vacuum oven (200 mm Hg) at room temperature for 20 minutes. The oven is then heated to 100° C. and the coating is cured for 2 hours under this condition. The heat of the oven is turned off and the slides are allowed to cool down to 50° C. in argon. Then the slides are cooled down to room temperature in ambient air. The slides are rinsed with MilliQ water twice in sonication bath, 2 minutes each time. Then the slides are dried in an IR heater for 15 minutes and then dried in the vacuum oven at 50° C. for 15 minutes.

Example 3: Preparation of an 8-Arm Polyethylene Glycol (PEG) Coating Functionalized with N-Hydroxysuccinimide (NHS) Groups on Glass Slides Microscope slides are cleaned with 2% Valtron SP2275 detergent in sonication bath heated to 60° C. Then they are dried in a vacuum oven at 100° C. for 30 minutes. A coating Solution A, the first solution, or active coating mixture, is prepared by mixing 10 mM (3-glycidyloxypropyl)trimethoxysilane (GOPS) and 5 mM 8arm-PEG-NH$_2$, hexaglycerol core in DMSO. The mixture is stirred for 30 minutes. In a separate vial, 40 mM N,N'-disuccinimidyl carbonate is dissolved in DMSO and the solution is added dropwise to the mixture containing GOPS and PEG (form Solution A). The first solution, Solution A, is stirred for additional 30 minutes. The second solution, coating Solution B, or the blocking mixture, is prepared by mixing 4.52 mM poly(ethylene glycol) sorbitol hexaoleate and 8.26 mM 6-azidosulfonylhexyltriethoxy silane in DMSO. The second solution, Solution B, mixture is stirred for 30 minutes. The Solution A and the Solution B are mixed in a 1 to 6 volume ratio. The mixture is stirred for 10 minutes and then diluted 1.2 times with DMSO. The final coating solution is filtered through a 0.2 μM DMSO-safe filter and dispenses 1 mL onto each microscope slide covering whole surface area. After allowing the coating solution wetting for 1 minute, the microscope slide is spun on the spin-coater using a two-step coating program (step 1: spin at 500 rpm for 10 seconds with acceleration of 100 rpm/s; step 2: spin at 4,000 rpm for 30 seconds with acceleration of 300 rpm/s). The coated slides are maintained in the vacuum oven (200 mm Hg) at room temperature for 20 minutes. The oven is then heated to 100° C. and the coating is cured for 2 hours under this condition. The heat of the oven is turned off and the slides are allowed to cool down to 50° C. in argon. Then the slides are cooled down to room temperature in ambient air. The slides are rinsed with MilliQ water twice in sonication bath, 2 minutes each time. Then the slides are dried in an IR heater for 15 minutes and then dried in the vacuum oven at 50° C. for 15 minutes.

Example 4: Preparation of a Low-Molecular-Weight Polyethylenimine (PEI) Coating Functionalized with N-Hydroxysuccinimide (NHS) Groups on Glass Slides Microscope slides are cleaned with 2% Valtron SP2275 detergent in sonication bath heated to 60° C. Then they are dried in a vacuum oven at 100° C. for 30 minutes. A coating Solution A or the active coating mixture, is prepared by mixing 10 mM (3-Glycidyloxypropyl)trimethoxysilane (GOPS) and 4 mM polyethylenimine (Mw.~800 Da) in DMSO. The mixture is stirred for 30 minutes. In a separate vial, 40 mM N,N'-disuccinimidyl carbonate is dissolved in DMSO and the solution is added dropwise to the mixture containing GOPS and PEI (form Solution A). The Solution A is stirred for additional 30 minutes. A coating Solution B or blocking mixture is prepared by mixing 4.52 mM poly(ethylene glycol) sorbitol hexaoleate and 8.26 mM 6-azidosulfonylhexyltriethoxy silane in DMSO. The Solution B mixture is stirred for 30 minutes. The Solution A and the Solution B are mixed in a 1 to 6 volume ratio. The mixture is stirred for 10 minutes and then diluted 1.2 times with DMSO. The final coating solution is filtered through a 0.2 μM DMSO-safe filter and dispenses 1 mL onto each microscope slide covering whole surface area. After allowing the coating solution wetting for 1 minute, the microscope slide is spun on the spin-coater using a two-step coating program (step 1: spin at 500 rpm for 10 seconds with acceleration of 100 rpm/s; step 2: spin at 4,000 rpm for 30 seconds with acceleration of 300 rpm/s). The coated slides are maintained in the vacuum oven (200 mm Hg) at room temperature for 20 minutes. The oven is then heated to 100° C. and the coating is cured for 2 hours under this condition. The heat of the oven is turned off and the slides are allowed to cool down to 50° C. in argon. Then the slides are cooled down to room temperature in ambient air. The slides are rinsed with MilliQ water twice in sonication bath, 2 minutes each time. Then the slides are dried in an IR heater for 15 minutes and then dried in the vacuum oven at 50° C. for 15 minutes.

Example 5: Preparation of a Polyamidoamine (PAMAM) Dendrimer Generation 3 Coating Functionalized with N-Hydroxysuccinimide (NHS) Groups on Polystyrene Polymer Slides The coating solution is prepared and subjected onto the polystyrene polymer slides as described in Example 1. Then the coated slides are maintained in the vacuum oven (200 mm Hg) at room temperature for 20 minutes. The oven is then heated to 70° C. and the coating is cured for 4 hours under this condition. The heat of the oven is turned off and the slides are allowed to cool down to 50° C. in argon. Then the slides are cooled down to room temperature in ambient air. The slides are rinsed with MilliQ water twice in sonication bath, 2 minutes each time. Then the slides are dried in an IR heater for 15 minutes and then dried in the vacuum oven at 50° C. for 15 minutes.

Example 6: Fabrication of a Glycan Microarray Containing 80 Natural Glycans

Glycan Microarray is a useful tool for investigation of protein-carbohydrate interaction. It can be a platform used for development of diagnostics and therapeutics targeting glycan-related markers in diseases, such as cancers and infectious diseases. Compared with protein-protein or DNA-protein interactions, protein-carbohydrate interaction is relatively weak. In order to enhance the binding affinity on array, glycan microarray needs multivalent display (clustering) of glycan probes on surface. For this purpose, a library containing 80 glycan probes (Table 1) representing the carbohydrate structures in mammalian was immobilized onto a glass slide coated with PAMAM dendrimer (generation 2) terminated with hydrazide functional groups (Example 2). Each glycan was dissolved in a Print Buffer containing 0.15 M sodium phosphate, 0.1% Glycerol, 0.01% SDS (pH 5.8) with 100 μM concentration and printed onto the slides using ~1 nL probe. The printing process was performed in 60% relative humidity. After printing the glycan immobilization can be enhanced by incubation at 50° C. for 12 hours or microwave treatment for 10 minutes.

Figures 5A, 5B:
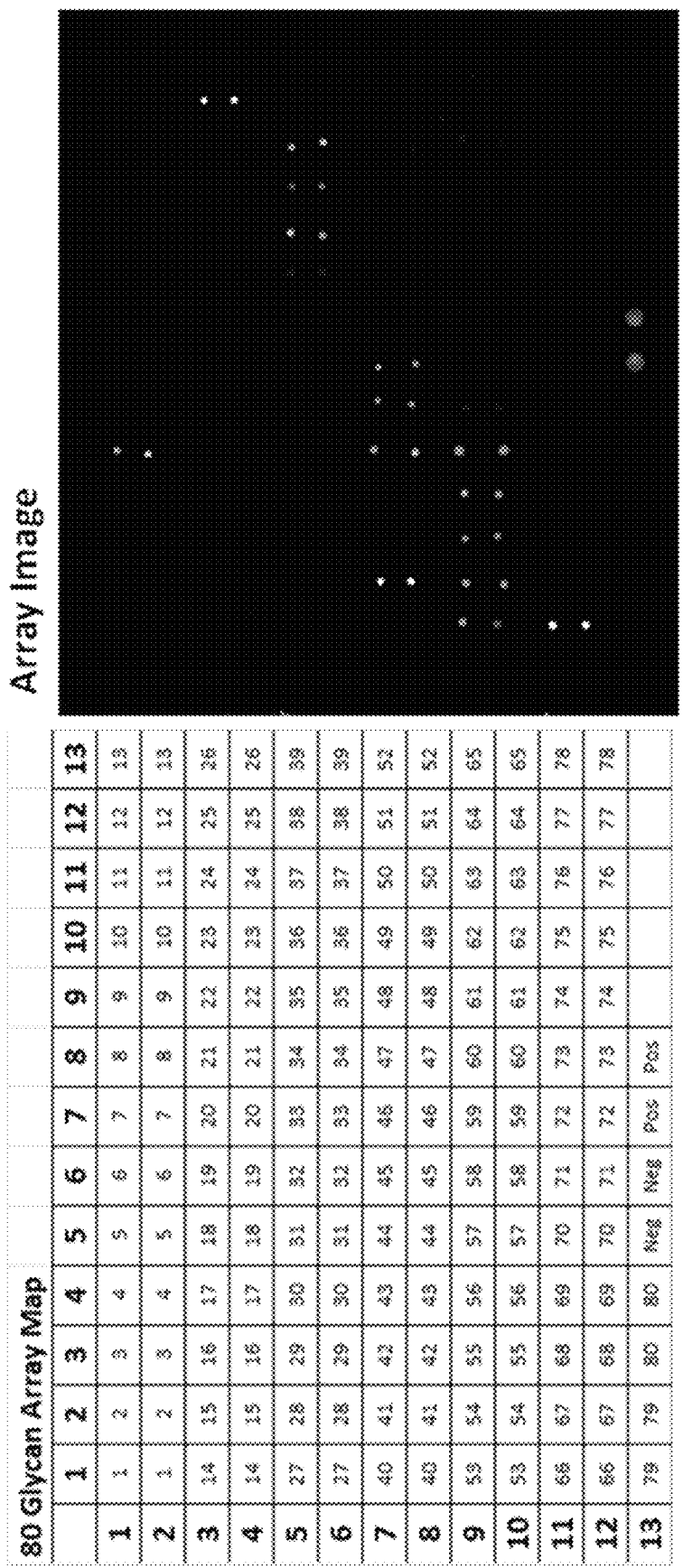
FIG. 5A illustrates the glycan map of an 80 Glycan Microarray. Numbers correspond to the list of glycans in Table 1.
FIG. 5B shows the array image for binding of *Aleuria aurantia* lectin (AAL) lectin (1 µg/ml) with affinity to fucose to a 80 Glycan Microarray and shows the glycan map. Numbers correspond to the list of glycans in Table 1
Figure 5C:
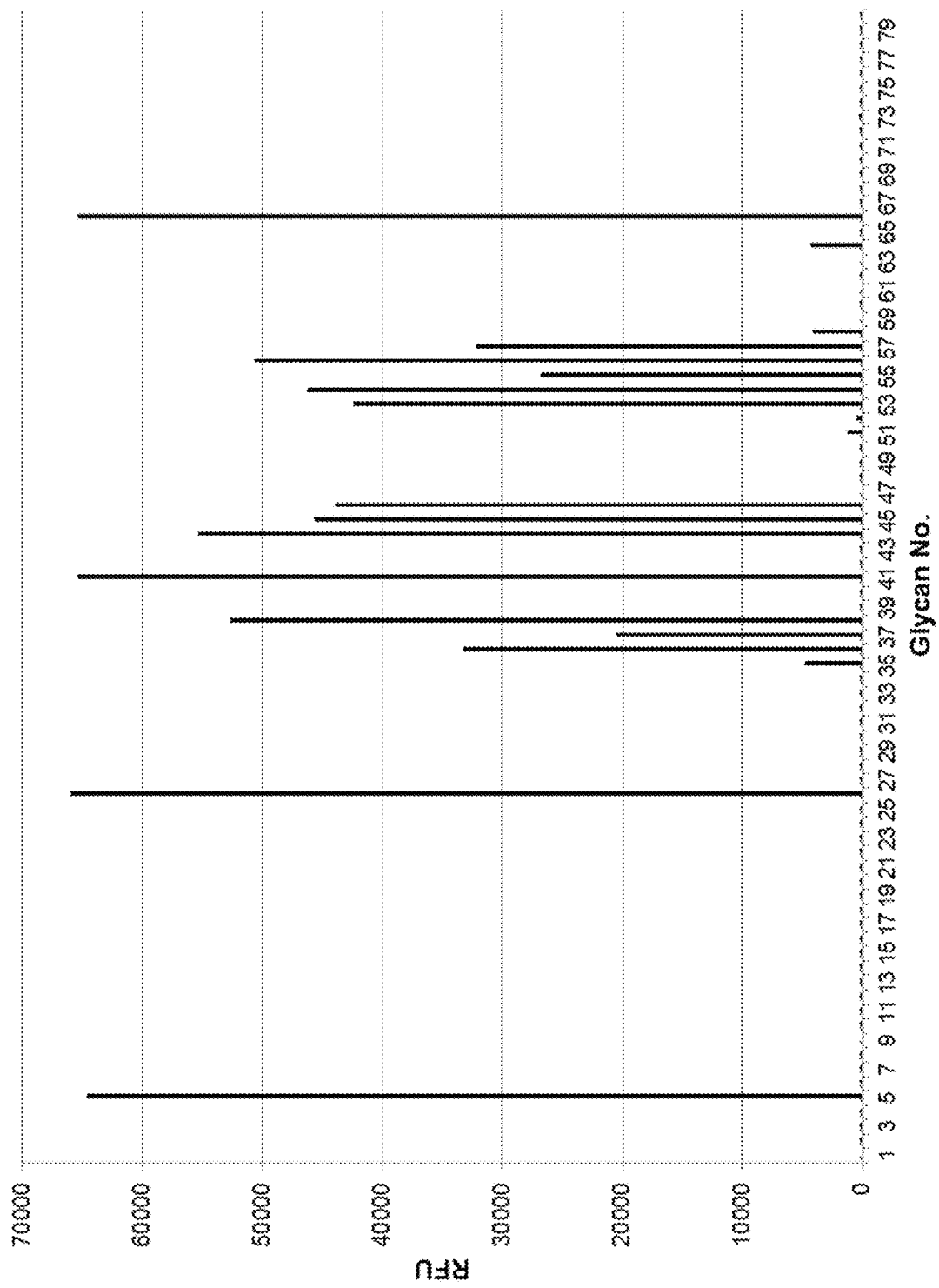
FIG. 5C illustrates the result for binding of AAL lectin (1 µg/ml) to a 80 Glycan Microarray in graphical format.

The carbohydrate-protein interaction can be investigated by interrogating the microarray with lectins or glycan-binding proteins. In detail, first the arrayed slides were briefly rinsed in MilliQ water and then affixed into an assay chamber. The arrays were treated with a blocking buffer, such as 1% BSA in PBST (PBS with 0.05% (v/v) Tween 20, pH 7.4). A biotinylated lectin (e.g., *Aleuria aurantia* Lectin (AAL)) or a glycan-binding protein (e.g., Cholera Toxin B subunit) dissolved in an Assay Buffer was subjected to the array for incubation. The Assay Buffer could be 20 mM Tris-HCl, 150 mM NaCl, 0.05% Tween 20, 1 mM CaCl$_2$), 1 mM MgCl$_2$, 1% BSA (pH 7.6). The protein-carbohydrate binding was detected by applying a Cy3 labeled streptavidin. The binding intensities—relative fluorescence units (RFU)—were quantified by using a fluorescence-based microarray scanner (FIG. 5A, FIG. 5B, FIG. 5C). The glycans containing L-fucose epitope showed as expected specific binding to the *Aleuria aurantia* lectin (AAL) lectin.

TABLE 1

| No. | Glycan Structure | Common Name |
|---|---|---|
| 1 | D-Mannose | D-Mannose |
| 2 | D-Glucose | D-Glucose |
| 3 | D-Fucose | D-Fucose |
| 4 | D-Galactose | D-Galactose |
| 5 | L-Fucose | L-Fucose |
| 6 | L-Rhamnose | L-Rhamnose |
| 7 | D-ManNAc | D-ManNAc |
| 8 | D-GlcNAc | D-GlcNAc |
| 9 | NeuNAc | Sialic acid |
| 10 | Fruc$\beta$2-1Glc$\alpha$ | Sucrose |
| 11 | Gal$\beta$1-4Glc | Lactose |
| 12 | Gal$\beta$1-4GlcNAc | LacNAc |
| 13 | Gal$\beta$1-3GlcNAc | Lac-N-biose |
| 14 | Gal$\beta$1-4Gal | 4-$\beta$-Galactobiose |
| 15 | GalNAc$\beta$1-3Gal | $\beta$-D-N-acetyl-galactosaminyl 1-3 galactose |
| 16 | Glc$\alpha$1-4Glc | Maltose |
| 17 | Glc$\beta$1-4Glc | Cellobiose |
| 18 | GlcNAc$\beta$1-4GlcNAc | Diacetylchitobiose |
| 19 | GlcNAc$\beta$1-2Man | $\beta$-D-N-acetylglucosaminyl 1-2 mannose |
| 20 | GlcNAc$\beta$1-4MurNAc | GlcNAcMurNAc |
| 21 | GlcNH$_2$$\beta$1-4GlcNH$_2$ | Chitobiose |
| 22 | Man$\alpha$1-2Man | 2-Mannbiose |
| 23 | Man$\alpha$1-3Man | 3-Mannobiose |
| 24 | Man$\alpha$1-4Man | 4-Mannobiose |
| 25 | Man$\alpha$1-6Man | 6-Mannobiose |
| 26 | Fuc$\alpha$1-2Gal | Blood H disacch |
| 27 | $\alpha$-$\Delta$UA-2S-[1-4]-GlcNS-6S | Heparin disaccharide |
| 28 | GlcNH$_2$$\beta$1-4GlcNH$_2$$\beta$1-4GlcNH2 | Chitotriose |
| 29 | Gal$\beta$1-4Gal$\beta$1-4Glc | Globotriose |
| 30 | GlcNAc$\beta$1-4GlcNAc$\beta$1-4GlcNAc | Triacetyl chitotriose |
| 31 | Neu5Ac$\alpha$2-3Gal$\beta$1-4Glc | 3'-SL |
| 32 | Neu5Ac$\alpha$2-6Gal$\beta$1-4Glc | 6'-SL |
| 33 | Neu5Ac$\alpha$2-3Gal$\beta$1-4GlcNAc | 3'-SLN |
| 34 | Neu5Ac$\alpha$2-6Gal$\beta$1-4GlcNAc | 6'-SLN |
| 35 | SO$_3$-3Gal$\beta$1-4-(Fuc1-3)GlcNAc | Sulpho-Lewis x |
| 36 | SO$_3$-3Gal$\beta$1-4-(Fuc1-4)-GlcNAc | Sulpho-Lewis a |
| 37 | Gal$\beta$1-4-(Fuc1-3)-GlcNAc | Lewis x Tri |
| 38 | Gal$\beta$1-3-(Fuc1-4)-GlcNAc | Lewis a Tri |
| 39 | Glc$\alpha$1-4Glc$\alpha$1-4Glc | Maltotriose |
| 40 | Glc$\beta$1-4Glc$\beta$1-4Glc | Cellotriose |
| 41 | Fuc$\alpha$1-2Gal$\beta$1-4Glc | 2'FL |
| 42 | Gal$\beta$1-3Gal$\beta$1-3GlcNAc | Linear B-2 Tri (Blood Group B Type 2 Linear Tri) |
| 43 | Gal$\alpha$1-4Gal$\beta$1-4GlcNAc | P1 antigen Tri |
| 44 | Fuc$\alpha$1-2Gal$\beta$1-3GlcNAc | Blood group H Tri |
| 45 | GalNAc$\alpha$1-3-(Fuc1-2)Gal | Blood group A Tri |
| 46 | Gal$\alpha$1-3-(Fuc1-2)Gal | Blood group B Tri |
| 47 | Gal$\beta$1-3GlcNAc$\beta$1-3Gal$\beta$1-4Glc | Lacto-N-tetraose (LNT) |
| 48 | Gal$\beta$1-4GlcNAc$\beta$1-3Gal$\beta$1-4Glc | Lacto-N-neotetraose (LNnT) |
| 49 | Gal$\beta$1-3Gal$\beta$1-4Gal$\beta$1-3Gal | Gal4 |
| 50 | Glc$\alpha$1-4Glc$\alpha$1-4Glc4Glc | Maltotetratose |
| 51 | Neu5Ac$\alpha$2-3Gal$\beta$1-4-(Fuc$\alpha$1-3)GlcNAc | Sialyl lewis x |
| 52 | Neu5Ac$\alpha$2-3Gal$\beta$1-3-(Fuc$\alpha$1-4)-GlcNAc | Sialyl lewis a |
| 53 | Fuc$\alpha$1-2Gal$\beta$1-3-(Fuc$\alpha$1-4)GlcNAc | Lewis b Tetra |
| 54 | Fuc$\alpha$1-2Gal$\beta$1-4-(Fuc$\alpha$1-3)GlcNAc | Lewis y Tetra |
| 55 | Fuc$\alpha$1-2Gal$\beta$1-3GlcNAc$\beta$1-3Gal$\beta$1-4Glc | Lacto-N-Fucopentaose I (LNFP-I) |
| 56 | Gal$\beta$1-3(Fuc$\alpha$1-4)GlcNAc$\beta$1-3Gal$\beta$1-4Glc | Lacto-N-Fucopentaose II (LNFP-II) |
| 57 | Gal$\beta$1-4(Fuc$\alpha$1-3)GlcNAc$\beta$1-3Gal$\beta$1-4Glc | Lacto-N-Fucopentaose III (LNFP-III) |
| 58 | Fuc$\alpha$1-2Gal$\beta$1-3Gal$\beta$1-4(Fuc$\alpha$1-3)Glc | B-Penta (Human Urine) |
| 59 | Glc$\alpha$1-4Glc$\alpha$1-4Glc$\alpha$1-4Glc | Maltopentaose |
| 60 | [Man$\alpha$1-3-(Man$\alpha$1-6)-Man$\alpha$1-6]-(Man$\alpha$1-3)-Man | Man5 |
| 61 | Neu5Ac$\alpha$2-6(Gal$\beta$1-3)GlcNAc$\beta$1-3Gal$\beta$1-4Glc | LS-Tetrasaccharide b (LsTb) |
| 62 | Neu5Ac$\alpha$2-6Gal$\beta$1-4GlcNAc$\beta$1-3Gal$\beta$1-4Glc | LS-Tetrasaccharide c (LsTc) |
| 63 | Gal$\beta$1-3GalNAc$\beta$1-4(Neu5Ac$\alpha$2-3)Gal$\beta$1-4Glc | GM1 Glycan |
| 64 | GalNAc$\alpha$1-3(Fuc$\alpha$1-2)Gal$\beta$1-4(Fuc$\alpha$1-3)Glc | Blood Group A Penta |
| 65 | (GlcNAc$\beta$1-2Man$\alpha$1)21-3,6Man | Bianntennary N-linked core pentasaccharide |
| 66 | Gal$\beta$1-3(Fuc$\alpha$1-4)GlcNAc$\beta$1-3Gal$\beta$1-4(Fuc$\alpha$1-3)Glc | Lacto-N-difucohexaose II (LNH) |
| 67 | Neu5Ac$\alpha$2-3Gal$\beta$1-3(Neu5Ac$\alpha$2-6)GlcNAc$\beta$1-3Gal$\beta$1-4Glc | DSLNT |
| 68 | GlcNAc$\beta$1-4GlcNAc$\beta$1-4GlcNAc$\beta$1-4GlcNAc$\beta$1-4GlcNAc$\beta$1-4GlcNAc | Hexaacetyl chitohexaose |
| 69 | Glc$\alpha$1-4Glc$\alpha$1-4Glc$\alpha$1-4Glc$\alpha$1-4Glc$\alpha$1-4Glc | Maltohexaose |
| 70 | Glc$\alpha$1-4Glc$\alpha$1-4Glc$\alpha$1-4Glc$\alpha$1-4Glc$\alpha$1-4Glc$\alpha$1-4Glc | Maltoheptaose |
| 71 | (4GlcUA$\beta$1-4GlcNAc(6S)$\alpha$1)4 | Heparin octasaccharide |
| 72 | [Man$\alpha$1-3-(Man$\alpha$1-6)-Man$\alpha$1-6]-(Man$\alpha$1-3)-Man$\beta$1-4GlcNAc$\beta$1-4GlcNAc | MAN-5; (Man)5(GlcNAc)2 |
| 73 | [(Man$\alpha$1-2Man$\alpha$1)2-3,6Man$\alpha$1-6]-(Man$\alpha$1-2Man$\alpha$1-2Man$\alpha$1-3)-Man$\beta$1-4GlcNAc$\beta$1-4GlcNAc | MAN-9; (Man)9(GlcNAc)2 |
| 74 | [(Man$\alpha$1)2-3,6Man$\alpha$1-6]-(Man$\alpha$1-2Man$\alpha$1-3)-Man$\beta$1-4GlcNAc$\beta$1-4GlcNAc | Oligomannose-6 (Man-6) |
| 75 | [(Man$\alpha$1)2-3,6Man$\alpha$1-6]-(Man$\alpha$1-2Man$\alpha$1-2Man$\alpha$1-3)-Man$\beta$1-4GlcNAc$\beta$1-4GlcNAc | Oligomannose-7D1 (Man-7D1) |
| 76 | [(Man$\alpha$1-2Man$\alpha$1)Man$\alpha$1-3,6Man$\alpha$1-6]-(Man$\alpha$1-2Man$\alpha$1-3)-Man$\beta$1-4GlcNAc$\beta$1-4GlcNAc | Oligomannose-7D3 (Man-7D3) |
| 77 | [(Man$\alpha$1-2Man$\alpha$1)Man$\alpha$1-3,6Man$\alpha$1-6]-(Man$\alpha$1-2Man$\alpha$1-2Man$\alpha$1-3)-Man$\beta$1-4GlcNAc$\beta$1-4GlcNAc | Oligomannose-8D1D3 (Man-8D1D3) |
| 78 | (Man$\alpha$1-6Man)n | Mannan |
| 79 | Lipopolysaccharides | E. coli LPS O111:B4 |
| 80 | (4GlcUA$\beta$1-3GalNAc$\beta$1)n | Chondroitin sulfate |

Example 7: Fabrication of a Glycan Microarray Containing 12 Synthetic Mucin 0-GalNAc Glycans For this purpose, a library containing 12 glycan probes representing 0-GalNAc glycan structures in mucin (Table 2) was immobilized onto a glass slide coated with PAMAM dendrimer (generation 2) terminated with NHS functional groups (Example 1). Each glycan was dissolved in a Print Buffer containing 150 mM sodium phosphate, (pH 8.5) with 100 μM concentration and printed onto the slides using ~1 nL probe. The printing process was performed in 60% relative humidity. After printing the glycan immobilization can be enhanced by incubation at room temperature for 12 hours in 60% relative humidity.

Figure 6:
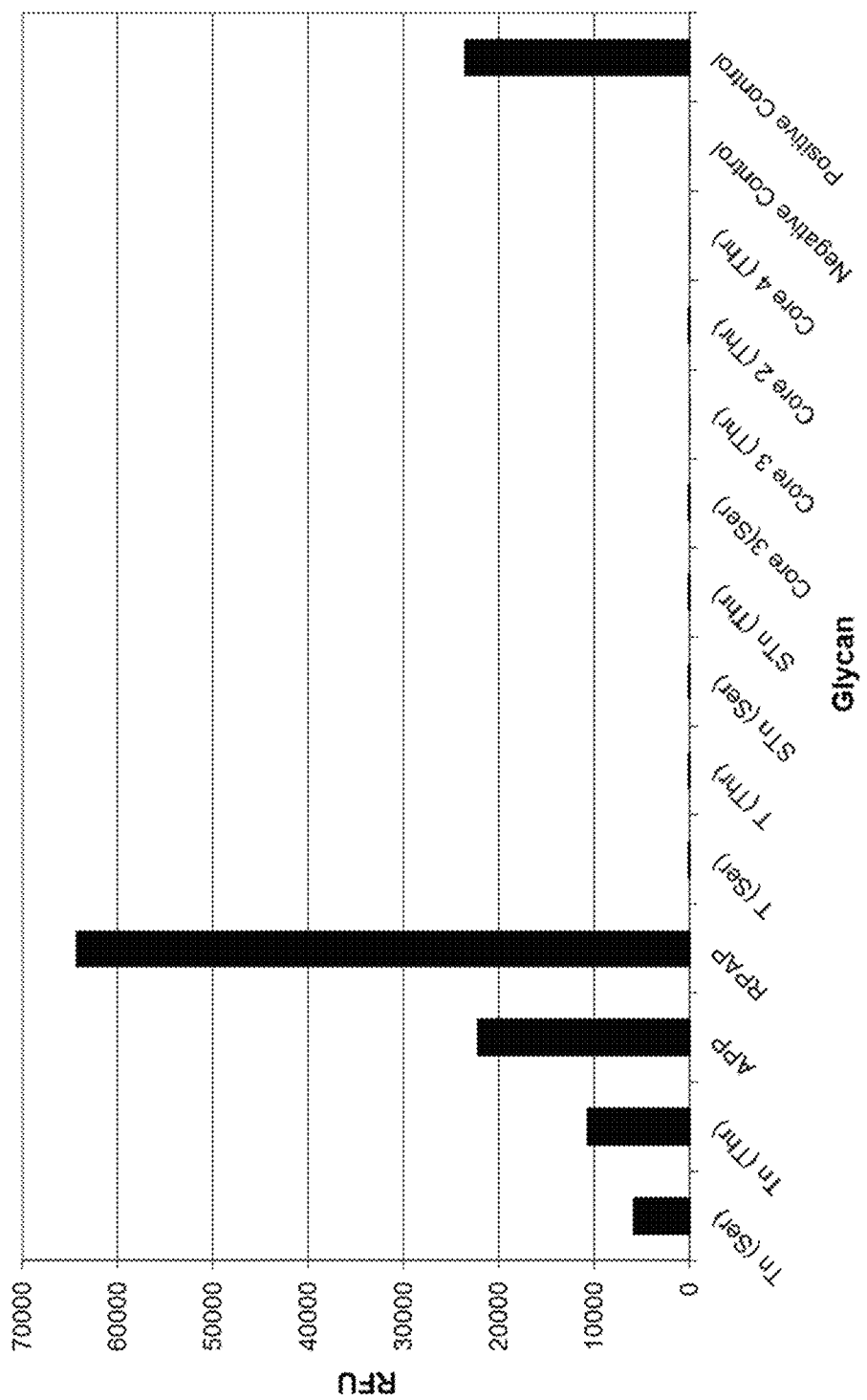
FIG. 6 illustrates an assay results for binding of Soybean agglutinins (SBA) lectin (1 µg/ml) to an O-mucin glycan microarray (Example 7) (glycans in assay shown in Table 2).

The carbohydrate-protein interaction can be investigated by interrogating the microarray with lectins or glycan-binding proteins. In detail, first the arrayed slides were briefly rinsed in MilliQ water and then affixed into an assay chamber. The arrays were treated with a blocking buffer, such as 25 mM ethanolamine in 100 mM boric acid, 0.01% Tween 20 (pH 8.5). A biotinylated lectin (e.g., *Helix pomatia* Agglutinin (HPA)) or a glycan-binding protein dissolved in an Assay Buffer was subjected to the array for incubation. The Assay Buffer could be 20 mM Tris-HCl, 150 mM NaCl, 0.05% Tween 20, 1 mM CaCl$_2$), 1 mM MgCl$_2$, 1% BSA (pH 7.6). The protein-carbohydrate binding was detected by applying a Cy3 labeled streptavidin. The binding intensities—relative fluorescence units (RFU)—were quantified by using a fluorescence-based microarray scanner (FIG. 6). The Soybean agglutinins (SBA) lectin showed as expected specific binding to the Tn antigens (Tn-Ser and Tn-Thr) and MUC-1 glycopeptides (APP and RPAP) containing terminal α-GalNAc epitope.

TABLE 2

| Glycan Structure | Common Name |
|---|---|
| α-GalNAc-Ser | Tn antigen (Ser) |
| α-GalNAc-Thr | Tn antigen (Thr) |
| H₂N-APGST*APP-NH2 (*α-GalNAc) | MUC-1 Glycopeptide APP |
| H₂N-TSAPDT*RPAP-NH2 (*α-GalNAc) | MUC-1 Glycopeptide RPAP |
| Galβ1-3GalNAcα1-Ser | T antigen (Ser) |
| Galβ1-3GalNAcα1-Thr | T antigen (Thr) |
| Neu5Acα2-6GalNAcα1-Ser | STn antigen (Ser) |
| Neu5Acα2-6GalNAcα1-Thr | STn antigen (Thr) |
| GlcNAcβ1-3GalNAcα1-Ser | Core 3 (Ser) |
| GlcNAcβ1-3GalNAcα1-Thr | Core 3 (Thr) |
| GlcNAcβ1-6(Galβ1-3)GalNAcα1-Thr | Core 2 (Thr) |
| GlcNAcβ1-6(GlcNAcβ1-3)GalNAcα1-Thr | Core 4 (Thr) |

Ser: serine
Thr: threonine

Figure 7:
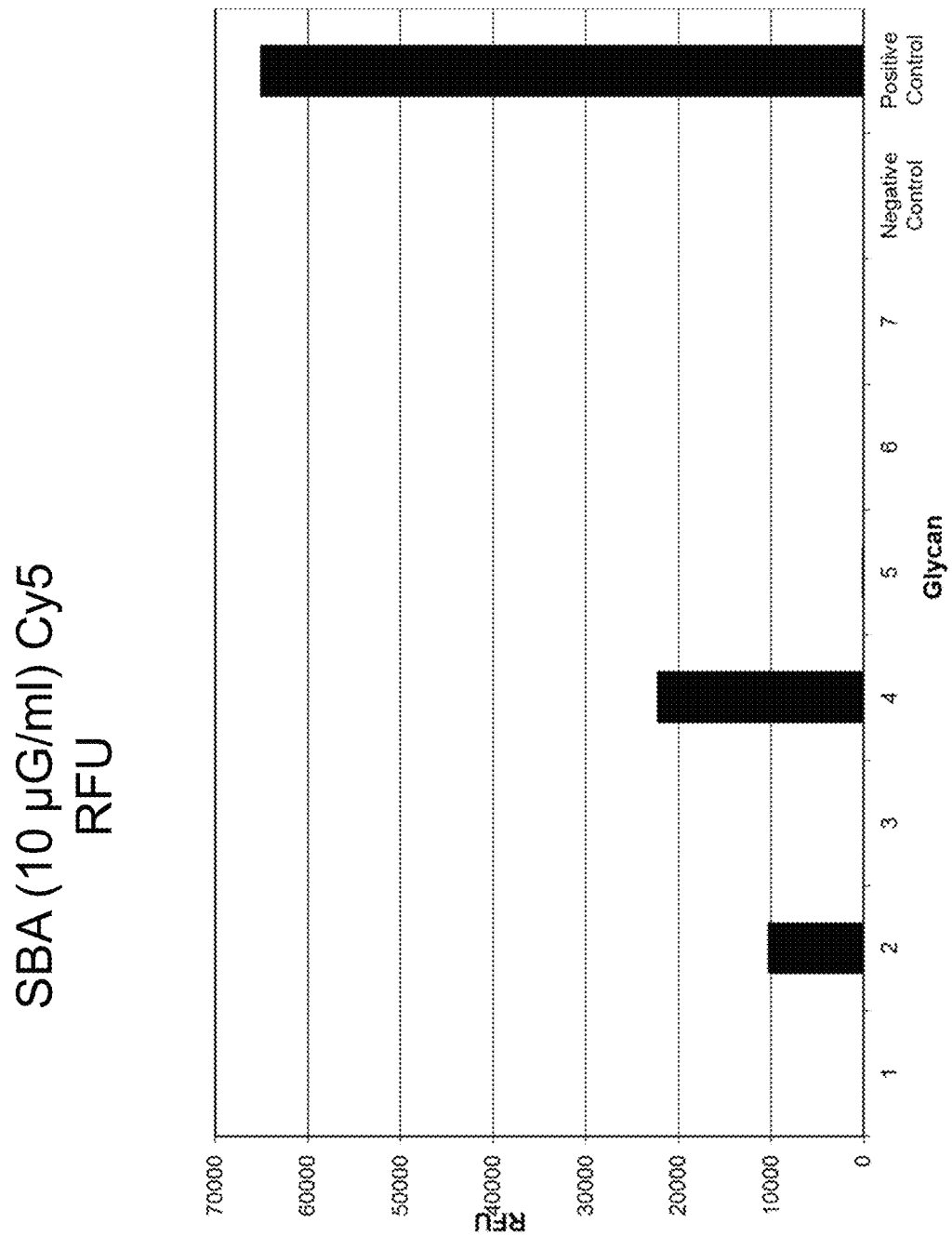
FIG. 7 illustrates assay results for binding of Soybean agglutinins (SBA, 10 µg/ml). (Example 5; glycans on assay shown in Table 3)
Figure 8:
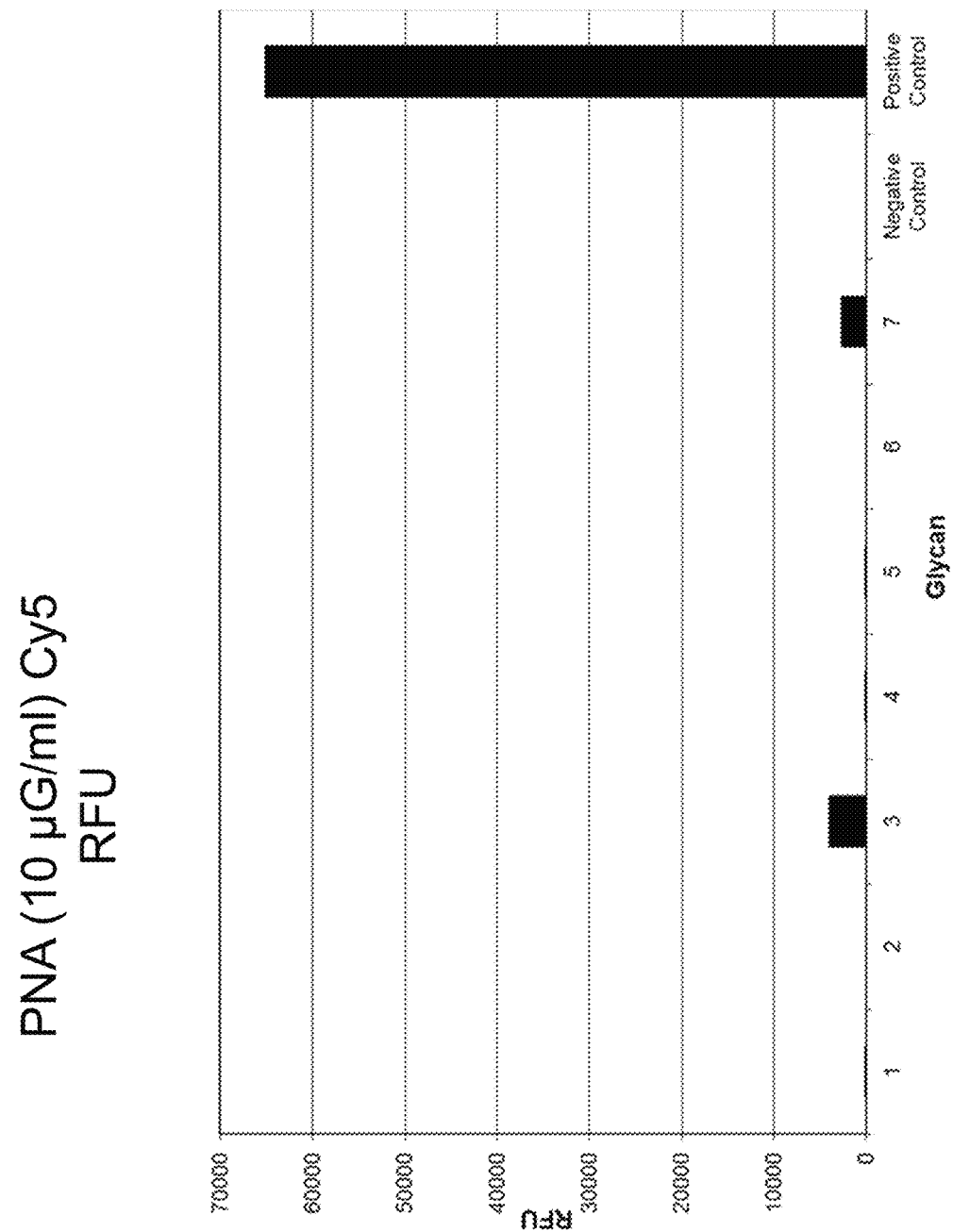
FIG. 8 illustrates assay results for binding of Peanut agglutinin (PNA, 10 µg/ml).
Figure 9:
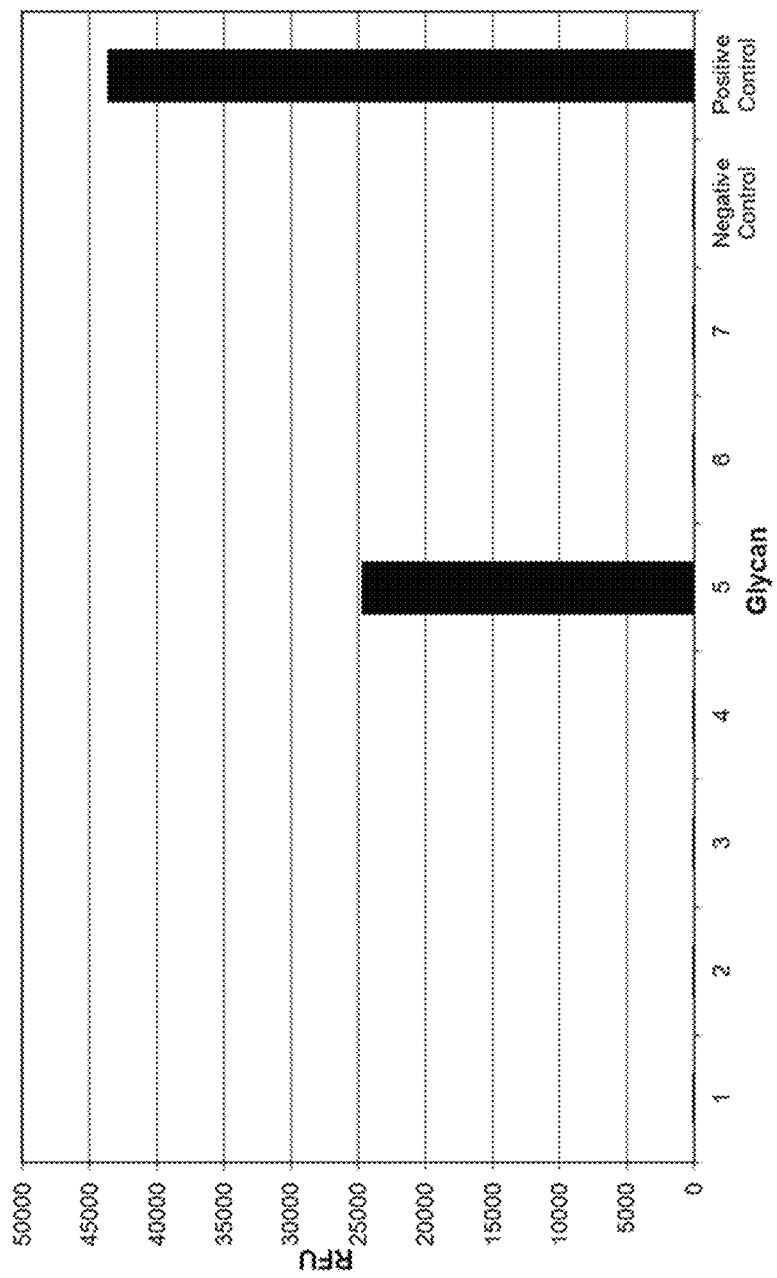
FIG. 9 illustrates assay results with ConA (1 µg/ml) lectins to a glycan array on polystyrene polymer slides (Example 5; glycans on assay shown in Table 3).

Example 8: Fabrication of a Glycan Microarray Containing 7 Synthetic Glycans (Table 3) on Polystyrene Polymer Slides Coated with Polyamidoamine (PAMAM) dendrimer generation 3 functionalized with N-hydroxysuccinimide (NHS) groups (Example 5). The glycan array was fabricated same as described in Example 7. Biotinylated lectins (e.g., SBA, FIG. 7; PNA, FIG. 8; and ConA, FIG. 9) were used for examine the binding on the glycan array by detection with a Cy5 labeled streptavidin. The soybean agglutinins (SBA) lectin showed as expected specific binding to the Tn antigen (Tn-Thr, No. 2) and the MUC-1 glycopeptide (APP, No. 4) containing terminal α-GalNAc epitope (FIG. 7). The peanut agglutinin (PNA) lectin showed as expected specific binding to the T antigens (T-Thr, No. 3 and T-Ser, No. 7) containing Galβ1-3GalNAcα epitope (FIG. 8). The ConA lectin showed as expected specific binding the high-mannose N-glycan (Man-9) containing mannose epitope (FIG. 9).

TABLE 3

| | Structure | Common Name |
|---|---|---|
| 1 | β-D-Gal-O—C₄H₈NH₂ | 4-aminobutyl β-D-galactopyranoside |
| 2 | α-GalNAc-Thr | Tn antigen (Thr) |
| 3 | Galβ1-3GalNAcα1-Thr | T antigen (Thr) |
| 4 | H₂N-APGST*APP-NH2 (*α-GalNAc) | MUC-1 Glycopeptide APP |
| 5 | [(Manα1-2Manα1)₂-3,6Manα1-6]-(Manα1-2Manα1-2Manα1-3)-Manβ1-4GlcNAcβ1-4GlcNAc | Man-9 N-glycan |
| 6 | α-GalNAc-Ser | Tn antigen |
| 7 | Galβ1-3GalNAcα1-Ser | T antigen |

Example 9

Comparison of the multivalent glycan substrate of the present invention to prior art AAL binding profiles of a glycan array printed with 100 N-glycans on hydrazide-functionalized multivalent substrate coated with aniline and slides coated without aniline, according to the methods disclosed in Example 6. N-glycans 1-100 are as follows in Table 4:

TABLE 4

| # | Name |
|---|---|
| 1 | (GlcNAcβ1-2Manα1-6(GlcNAcβ1-2Manα1-3)Manβ1-4GlcNAcβ1-4GlcNAc- |
| 2 | Galβ1-4GlcNAcβ1-2Manα1-6(Galβ1-4GlcNAcβ1-2Manα1-3)Manβ1-4GlcNAcβ1-4GlcNAc- |
| 3 | Neu5Acα2-3Galβ1-4GlcNAcβ1-2Manα1-6(Neu5Acα2-3Galβ1-4GlcNAcβ1-2Manα1-3)Manβ1-4GlcNAcβ1-4GlcNAc- |
| 4 | Neu5Acα2-6Galβ1-4GlcNAcβ1-2Manα1-6(Neu5Acα2-6Galβ1-4GlcNAcβ1-2Manα1-3)Manβ1-4GlcNAcβ1-4GlcNAc- |
| 5 | Galβ1-4(Fucα1-3)GlcNAcβ1-2Manα1-6(Galβ1-4(Fucα1-3)GlcNAcβ1-2Manα1-3)Manβ1-4GlcNAcβ1-4GlcNAc- |
| 6 | Neu5Acα2-3Galβ1-4(Fucα1-3)GlcNAcβ1-2Manα1-6(Neu5Acα2-3Galβ1-4(Fucα1-3)GlcNAcβ1-2Manα1-3)Manβ1-4GlcNAcβ1-4GlcNAc- |
| 7 | Manα1-6(Manα1-3)Manα1-6(GlcNAcβ1-2Manα1-3)Manβ1-4GlcNAcβ1-4GlcNAc- |
| 8 | Manα1-6(Manα1-3)Manα1-6(Galβ1-4GlcNAcβ1-2Manα1-3)Manβ1-4GlcNAcβ1-4GlcNAc- |
| 9 | Manα1-6(Manα1-3)Manα1-6(Neu5Acα2-3Galβ1-4GlcNAcβ1-2Manα1-3)Manβ1-4GlcNAcβ1-4GlcNAc- |
| 10 | Manα1-6(Manα1-3)Manα1-6(Neu5Acα2-6Galβ1-4GlcNAcβ1-2Manα1-3)Manβ1-4GlcNAcβ1-4GlcNAc- |
| 11 | Manα1-6(Manα1-3)Manα1-6(Galβ1-4(Fucα1-3)GlcNAcβ1-2Manα1-3)Manβ1-4GlcNAcβ1-4GlcNAc |
| 12 | Manα1-6(Manα1-3)Manα1-6(Neu5Acα2-3Galβ1-4(Fucα1-3)GlcNAcβ1-2Manα1-3)Manβ1-4GlcNAcβ1-4GlcNAc- |
| 13 | GlcNAcβ1-2Manα1-3Manβ1-4GlcNAcβ1-4GlcNAc- |
| 14 | Galβ1-4GlcNAcβ1-2Manα1-3Manβ1-4GlcNAcβ1-4GlcNAc- |
| 15 | Neu5Acα2-3Galβ1-4GlcNAcβ1-2Manα1-3Manβ1-4GlcNAcβ1-4GlcNAc- |
| 16 | Neu5Acα2-6Galβ1-4GlcNAcβ1-2Manα1-3Manβ1-4GlcNAcβ1-4GlcNAc- |
| 17 | Galβ1-4(Fucα1-3)GlcNAcβ1-2Manα1-3Manβ1-4GlcNAcβ1-4GlcNAc- |
| 18 | Neu5Acα2-3Galβ1-4(Fucα1-3)GlcNAcβ1-2Manα1-3Manβ1-4GlcNAcβ1-4GlcNAc- |
| 19 | Manα1-6(GlcNAcβ1-2Manα1-3)Manβ1-4GlcNAcβ1-4GlcNAc- |
| 20 | Manα1-6(Galβ1-4GlcNAcβ1-2Manα1-3)Manβ1-4GlcNAcβ1-4GlcNAc- |

TABLE 4-continued

| # | Name |
|---|------|
| 21 | Manα1-6(Neu5Acα2-3Galβ1-4GlcNAcβ1-2Manα1-3)Manβ1-4GlcNAcβ1-4GlcNAc- |
| 22 | Manα1-6(Neu5Acα2-6Galβ1-4GlcNAcβ1-2Manα1-3)Manβ1-4GlcNAcβ1-4GlcNAc- |
| 23 | Manα1-6(Galβ1-4(Fucα1-3)GlcNAcβ1-2Manα1-3)Manβ1-4GlcNAcβ1-4GlcNAc- |
| 24 | Manα1-6(Neu5Acα2-3Galβ1-4(Fucα1-3)GlcNAcβ1-2Manα1-3)Manβ1-4GlcNAcβ1-4GlcNAc- |
| 25 | GlcNAcβ1-2Manα1-6Manβ1-4GlcNAcβ1-4GlcNAc- |
| 26 | Galβ1-4GlcNAcβ1-2Manα1-6Manβ1-4GlcNAcβ1-4GlcNAc- |
| 27 | Neu5Acα2-3Galβ1-4GlcNAcβ1-2Manα1-6Manβ1-4GlcNAcβ1-4GlcNAc- |
| 28 | Neu5Acα2-6Galβ1-4GlcNAcβ1-2Manα1-6Manβ1-4GlcNAcβ1-4GlcNAc- |
| 29 | Galβ1-4(Fucα1-3)GlcNAcβ1-2Manα1-6Manβ1-4GlcNAcβ1-4GlcNAc- |
| 30 | Neu5Acα2-3Galβ1-4(Fucα1-3)GlcNAcβ1-2Manα1-6Manβ1-4GlcNAcβ1-4GlcNAc- |
| 31 | GlcNAcβ1-2Manα1-6(Manα1-3)Manβ1-4GlcNAcβ1-4GlcNAc- |
| 32 | Galβ1-4GlcNAcβ1-2Manα1-6(Manα1-3)Manβ1-4GlcNAcβ1-4GlcNAc- |
| 33 | Neu5Acα2-3Galβ1-4GlcNAcβ1-2Manα1-6(Manα1-3)Manβ1-4GlcNAcβ1-4GlcNAc- |
| 34 | Neu5Acα2-6Galβ1-4GlcNAcβ1-2Manα1-6(Manα1-3)Manβ1-4GlcNAcβ1-4GlcNAc- |
| 35 | Galβ1-4(Fucα1-3)GlcNAcβ1-2Manα1-6(Manα1-3)Manβ1-4GlcNAcβ1-4GlcNAc- |
| 36 | Neu5Acα2-3Galβ1-4(Fucα1-3)GlcNAcβ1-2Manα1-6(Manα1-3)Manβ1-4GlcNAcβ1-4GlcNAc- |
| 37 | (OAc)4GlcNAcβ1-2Manα1-6(GlcNAcβ1-2Manα1-3)Manβ1-4GlcNAcβ1-4GlcNAc- |
| 38 | GlcNAcβ1-2Manα1-6(Galβ1-4GlcNAcβ1-2Manα1-3)Manβ1-4GlcNAcβ1-4GlcNAc- |
| 39 | GlcNAcβ1-2Manα1-6(Neu5Acα2-3Galβ1-4GlcNAcβ1-2Manα1-3)Manβ1-4GlcNAcβ1-4GlcNAc- |
| 40 | GlcNAcβ1-2Manα1-6(Neu5Acα2-6Galβ1-4GlcNAcβ1-2Manα1-3)Manβ1-4GlcNAcβ1-4GlcNAc- |
| 41 | GlcNAcβ1-2Manα1-6(Galβ1-4(Fucα1-3)GlcNAcβ1-2Manα1-3)Manβ1-4GlcNAcβ1-4GlcNAc- |
| 42 | GlcNAcβ1-2Manα1-6(Neu5Acα2-3Galβ1-4(Fucα1-3)GlcNAcβ1-2Manα1-3)Manβ1-4GlcNAcβ1-4GlcNAc- |
| 43 | Galβ1-4GlcNAcβ1-2Manα1-6(Neu5Acα2-3Galβ1-4GlcNAcβ1-2Manα1-3)Manβ1-4GlcNAcβ1-4GlcNAc- |
| 44 | Galβ1-4GlcNAcβ1-2Manα1-6(Neu5Acα2-6Galβ1-4GlcNAcβ1-2Manα1-3)Manβ1-4GlcNAcβ1-4GlcNAc- |
| 45 | Galβ1-4GlcNAcβ1-2Manα1-6(Galβ1-4(Fucα1-3)GlcNAcβ1-2Manα1-3)Manβ1-4GlcNAcβ1-4GlcNAc- |
| 46 | Galβ1-4GlcNAcβ1-2Manα1-6(Neu5Acα2-3Galβ1-4(Fucα1-3)GlcNAcβ1-2Manα1-3)Manβ1-4GlcNAcβ1-4GlcNAc- |
| 47 | Neu5Acα2-3Galβ1-4GlcNAcβ1-2Manα1-6(Neu5Acα2-6Galβ1-4GlcNAcβ1-2Manα1-3)Manβ1-4GlcNAcβ1-4GlcNAc- |
| 48 | Neu5Acα2-3Galβ1-4GlcNAcβ1-2Manα1-6(Galβ1-4(Fucα1-3)GlcNAcβ1-2Manα1-3)Manβ1-4GlcNAcβ1-4GlcNAc- |
| 49 | Neu5Acα2-3Galβ1-4GlcNAcβ1-2Manα1-6(Neu5Acα2-3Galβ1-4(Fucα1-3)GlcNAcβ1-2Manα1-3)Manβ1-4GlcNAcβ1-4GlcNAc- |
| 50 | Neu5Acα2-6Galβ1-4GlcNAcβ1-2Manα1-6(Galβ1-4(Fucα1-3)GlcNAcβ1-2Manα1-3)Manβ1-4GlcNAcβ1-4GlcNAc- |
| 51 | Galβ1-4(Fucα1-3)GlcNAcβ1-2Manα1-6(Neu5Acα2-3Galβ1-4(Fucα1-3)GlcNAcβ1-2Manα1-3)Manβ1-4GlcNAcβ1-4GlcNAc- |
| 52 | GlcNAcβ1-2Manα1-6((OAc)4GlcNAcβ1-2)Manα1-3)Manβ1-4GlcNAcβ1-4GlcNAc- |
| 53 | Galβ1-4GlcNAcβ1-2Manα1-6(GlcNAcβ1-2Manα1-3)Manβ1-4GlcNAcβ1-4GlcNAc- |
| 54 | Neu5Acα2-3Galβ1-4GlcNAcβ1-2Manα1-6(GlcNAcβ1-2Manα1-3)Manβ1-4GlcNAcβ1-4GlcNAc- |
| 55 | Neu5Acα2-6Galβ1-4GlcNAcβ1-2Manα1-6(GlcNAcβ1-2Manα1-3)Manβ1-4GlcNAcβ1-4GlcNAc- |
| 56 | Galβ1-4(Fucα1-3)GlcNAcβ1-2Manα1-6(GlcNAcβ1-2Manα1-3)Manβ1-4GlcNAcβ1-4GlcNAc- |
| 57 | Neu5Acα2-3Galβ1-4(Fucα1-3)GlcNAcβ1-2Manα1-6(GlcNAcβ1-2Manα1-3)Manβ1-4GlcNAcβ1-4GlcNAc- |
| 58 | Neu5Acα2-3Galβ1-4GlcNAcβ1-2Manα1-6(Galβ1-4GlcNAcβ1-2Manα1-3)Manβ1-4GlcNAcβ1-4GlcNAc |
| 59 | Neu5Acα2-6Galβ1-4GlcNAcβ1-2Manα1-6(Galβ1-4GlcNAcβ1-2Manα1-3)Manβ1-4GlcNAcβ1-4GlcNAc- |
| 60 | Galβ1-4(Fucα1-3)GlcNAcβ1-2Manα1-6(Galβ1-4GlcNAcβ1-2Manα1-3)Manβ1-4GlcNAcβ1-4GlcNAc- |
| 61 | Neu5Acα2-3Galβ1-4(Fucα1-3)GlcNAcβ1-2Manα1-6(Galβ1-4GlcNAcβ1-2Manα1-3)Manβ1-4GlcNAcβ1-4GlcNAc- |
| 62 | Neu5Acα2-6Galβ1-4GlcNAcβ1-2Manα1-6(Neu5Acα2-3Galβ1-4GlcNAcβ1-2Manα1-3)Manβ1-4GlcNAcβ1-4GlcNAc- |

TABLE 4-continued

| # | Name |
|---|---|
| 63 | Galβ1-4(Fucα1-3)GlcNAcβ1-2Manα1-6(Neu5Acα2-3Galβ1-4GlcNAcβ1-2Manα1-3)Manβ1-4GlcNAcβ1-4GlcNAc- |
| 64 | Galβ1-4(Fucα1-3)GlcNAcβ1-2Manα1-6(Neu5Acα2-6Galβ1-4GlcNAcβ1-2Manα1-3)Manβ1-4GlcNAcβ1-4GlcNAc |
| 65 | Neu5Acα2-3Galβ1-4(Fucα1-3)GlcNAcβ1-2Manα1-6(Galβ1-4(Fucα1-3)GlcNAcβ1-2Manα1-3)Manβ1-4GlcNAcβ1-4GlcNAc- |
| 66 | GlcNAcβ1-2Manα1-6(GlcNAcβ1-2Manα1-3)Manβ1-4GlcNAcβ1-4(Fucα1-6)GlcNAc- |
| 67 | Manα1-6(GlcNAcβ1-2Manα1-3)Manβ1-4GlcNAcβ1-4(Fucα1-6)GlcNAc- |
| 68 | GlcNAcβ1-2Manα1-6(Galβ1-4GlcNAcβ1-2Manα1-3)Manβ1-4GlcNAcβ1-4(Fucα1-6)GlcNAc- |
| 69 | GlcNAcβ1-2Manα1-6(Neu5Acα2-3Galβ1-4GlcNAcβ1-2Manα1-3)Manβ1-4GlcNAcβ1-4(Fucα1-6)GlcNAc- |
| 70 | GlcNAcβ1-2Manα1-6(Neu5Acα2-6Galβ1-4GlcNAcβ1-2Manα1-3)Manβ1-4GlcNAcβ1-4(Fucα1-6)GlcNAc- |
| 71 | Galβ1-4GlcNAcβ1-2Manα1-6(Neu5Acα2-3Galβ1-4GlcNAcβ1-2Manα1-3)Manβ1-4GlcNAcβ1-4(Fucα1-6)GlcNAc |
| 72 | Galβ1-4GlcNAcβ1-2Manα1-6(Neu5Acα2-6Galβ1-4GlcNAcβ1-2Manα1-3)Manβ1-4GlcNAcβ1-4(Fucα1-6)GlcNAc- |
| 73 | Neu5Acα2-6Galβ1-4GlcNAcβ1-2Manα1-6(Galβ1-4(Fucα1-3)GlcNAcβ1-2Manα1-3)Manβ1-4GlcNAcβ1-4(Fucα1-6)GlcNAc- |
| 74 | Galβ1-4GlcNAcβ1-2Manα1-6(GlcNAcβ1-2Manα1-3)Manβ1-4GlcNAcβ1-4(Fucα1-6)GlcNAc |
| 75 | Neu5Acα2-3Galβ1-4GlcNAcβ1-2Manα1-6(GlcNAcβ1-2Manα1-3)Manβ1-4GlcNAcβ1-4(Fucα1-6)GlcNAc- |
| 76 | Neu5Acα2-6Galβ1-4GlcNAcβ1-2Manα1-6(GlcNAcβ1-2Manα1-3)Manβ1-4GlcNAcβ1-4(Fucα1-6)GlcNAc- |
| 77 | Neu5Acα2-3Galβ1-4GlcNAcβ1-2Manα1-6(Galβ1-4GlcNAcβ1-2Manα1-3)Manβ1-4GlcNAcβ1-4(Fucα1-6)GlcNAc- |
| 78 | Neu5Acα2-6Galβ1-4GlcNAcβ1-2Manα1-6(Galβ1-4GlcNAcβ1-2Manα1-3)Manβ1-4GlcNAcβ1-4(Fucα1-6)GlcNAc- |
| 79 | Galβ1-4(Fucα1-3)GlcNAcβ1-2Manα1-6(Neu5Acα2-6Galβ1-4GlcNAcβ1-2Manα1-3)Manβ1-4GlcNAcβ1-4(Fucα1-6)GlcNAc- |
| 80 | Galβ1-4GlcNAcβ1-2Manα1-6(Galβ1-4GlcNAcβ1-2(Galβ1-4GlcNAcβ1-4)Manα1-3)Manβ1-4GlcNAcβ1-4GlcNAc- |
| 81 | Galβ1-4(Fucα1-3)GlcNAcβ1-2Manα1-6(Galβ1-4(Fucα1-3)GlcNAcβ1-2(Galβ1-4(Fucα1-3)GlcNAcβ1-4)Manα1-3)Manβ1-4GlcNAcβ1-4GlcNAc- |
| 82 | Manβ1-4GlcNAcβ1-4GlcNAc- |
| 83 | Manα1-6Manβ1-4GlcNAcβ1-4GlcNAc- |
| 84 | Manα1-3Manβ1-4GlcNAcβ1-4GlcNAc- |
| 85 | Manα1-6(Manα1-3)Manβ1-4GlcNAcβ1-4GlcNAc- |
| 86 | Menα1-6(Manα1-3)Manα1-6(Manα1-3)Manβ1-4GlcNAcβ1-4GlcNAc- |
| 87 | Manα1-6(Manα1-3)Manα1-6(Manα1-2Manα1-3)Manβ1-4GlcNAcβ1-4GlcNAc- |
| 88 | Manα1-6(Manα1-2Manα1-3)Manα1-6(Manα1-3)Manβ1-4GlcNAcβ1-4GlcNAc- |
| 89 | [Manα1-2]Manα1-6(Manα1-3)Manα1-6(Manα1-2Manα1-3)Manβ1-4GlcNAcβ1-4GlcNAc-(3 isomers) |
| 90 | [Manα1-2] [Manα1-2] Manα1-6(Manα1-3)Manα1-6(Manα1-2Manα1-3)Manβ1-4GlcNAcβ1-4GlcNAc-(3 isomers) |
| 91 | Manα1-2Manα1-6(Manα1-2Manα1-3)Manα1-6(Manα1-2Manα1-2Manα1-3)Manβ1-4GlcNAcβ1-4GlcNAc- |
| 92 | Neu5Gcα2-3Galβ1-4GlcNAcβ1-2Manα1-6(Neu5Gcα2-3Galβ1-4GlcNAcβ1-2Manα1-3)Manβ1-4GlcNAcβ1-4GlcNAc- |
| 93 | Neu5Gcα2-6Galβ1-4GlcNAcβ1-2Manα1-6(Neu5Gcα2-6Galβ1-4GlcNAcβ1-2Manα1-3)Manβ1-4GlcNAcβ1-4GlcNAc- |
| 94 | Manα1-6(Manα1-3)Manα1-6(Neu5Gcα2-3Galβ1-4GlcNAcβ1-2Manα1-3)Manβ1-4GlcNAcβ1-4GlcNAc- |
| 95 | Manα1-6(Manα1-3)Manα1-6(Neu5Gcα2-6Galβ1-4GlcNAcβ1-2Manα1-3)Manβ1-4GlcNAcβ1-4GlcNAc- |
| 96 | Manα1-6(Manα1-3)Manα1-6(Neu5Gcα2-3Galβ1-4(Fucα1-3)GlcNAcβ1-2Manα1-3)Manβ1-4GlcNAcβ1-4GlcNAc |
| 97 | Neu5Gcα2-3Galβ1-4GlcNAcβ1-2Manα1-3Manβ1-4GlcNAcβ1-4GlcNAc- |
| 98 | Neu5Gcα2-3Galβ1-4(Fucα1-3)GlcNAcβ1-2Manα1-3Manβ1-4GlcNAcβ1-4GlcNAc |
| 99 | GlcNAcβ1-2Manα1-6(Neu5Gcα2-3Galβ1-4GlcNAcβ1-2Manα1-3)Manβ1-4GlcNAcβ1-4GlcNAc- |
| 100 | GlcNAcβ1-2Manα1-6(Neu5Gcα2-6Galβ1-4GlcNAcβ1-2Manα1-3)Manβ1-4GlcNAcβ1-4GlcNAc- |

The results showed that the following glycans #11, 24, 29, 41, 42, 45, 46, 48, 49, 50, 51, 63-79, 96, 98 in Table 4, especially the biantennary complex N-glycans with internal α1,6-fucose (glycans #66-79), show great sensitivity enhancement on slides coated with aniline. See FIG. 10A. FIG. 10(B) shows the 2G12 antibody dynamic curve for binding to high-mannose N-glycan (Man-8) (glycan #90). 2G12 is pre-complexed with Cy3 labeled anti-Human IgG (1:4 ratio). The glycan showed greater sensitivity enhancement on the substrate coated with aniline than the subtracted without aniline coating. FIG. 10C shows the high-mannose N-glycan (Man-9) (glycan #91). 2G12 is pre-complexed with Cy3 labeled anti-Human IgG (1:4 ratio). The glycan showed greater sensitivity enhancement on the substrate coated with aniline than the subtracted without aniline coating. FIG. 10D shows CD15 (Lewis X) antibody dynamic curve for binding to a complex N-glycan (glycan #29 in Table 4). CD15 antibody is detected with Alexa Fluor 555-labeled anti-mouse IgM secondary antibody. The data from this week binding event shows the aniline substrate's advantage for detecting weak binding signal. The aniline can serve as a catalyst to increase aldehyde-hydrazide coupling efficiency, thus enhance the immobilization capability for glycans containing free reducing-end. The use of aniline as a nucleophilic catalyst accelerates bond formation through a Schiff base intermediate (mechanism in FIG. 4D).

Figure 10A:
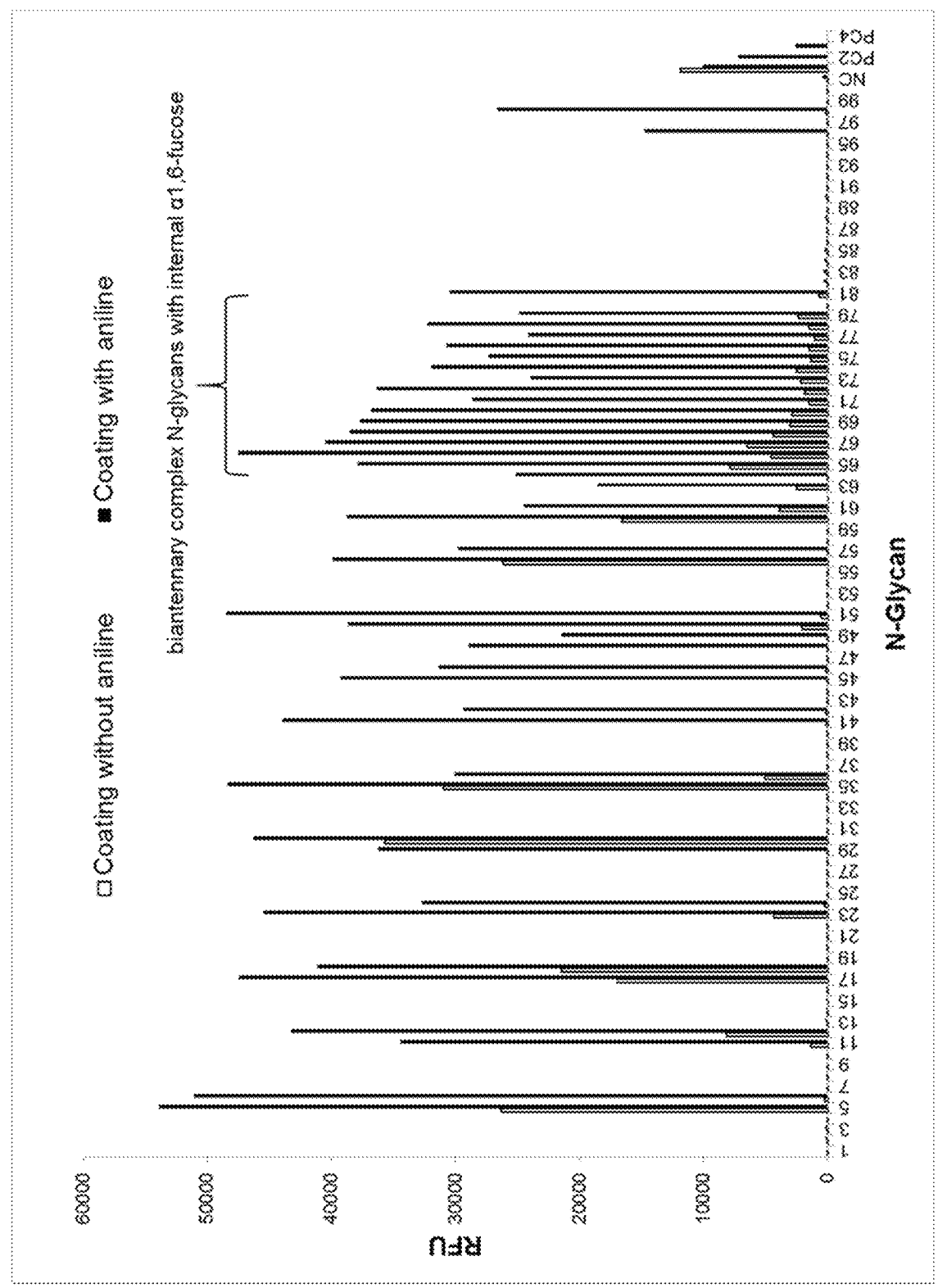
FIG. 10A illustrates AAL binding profiles of a glycan array printed with 100 N-glycans on hydrazide-functionalized multivalent substrate coated with aniline (solid bars) and slides coated without aniline (open bars).
Figure 10B:
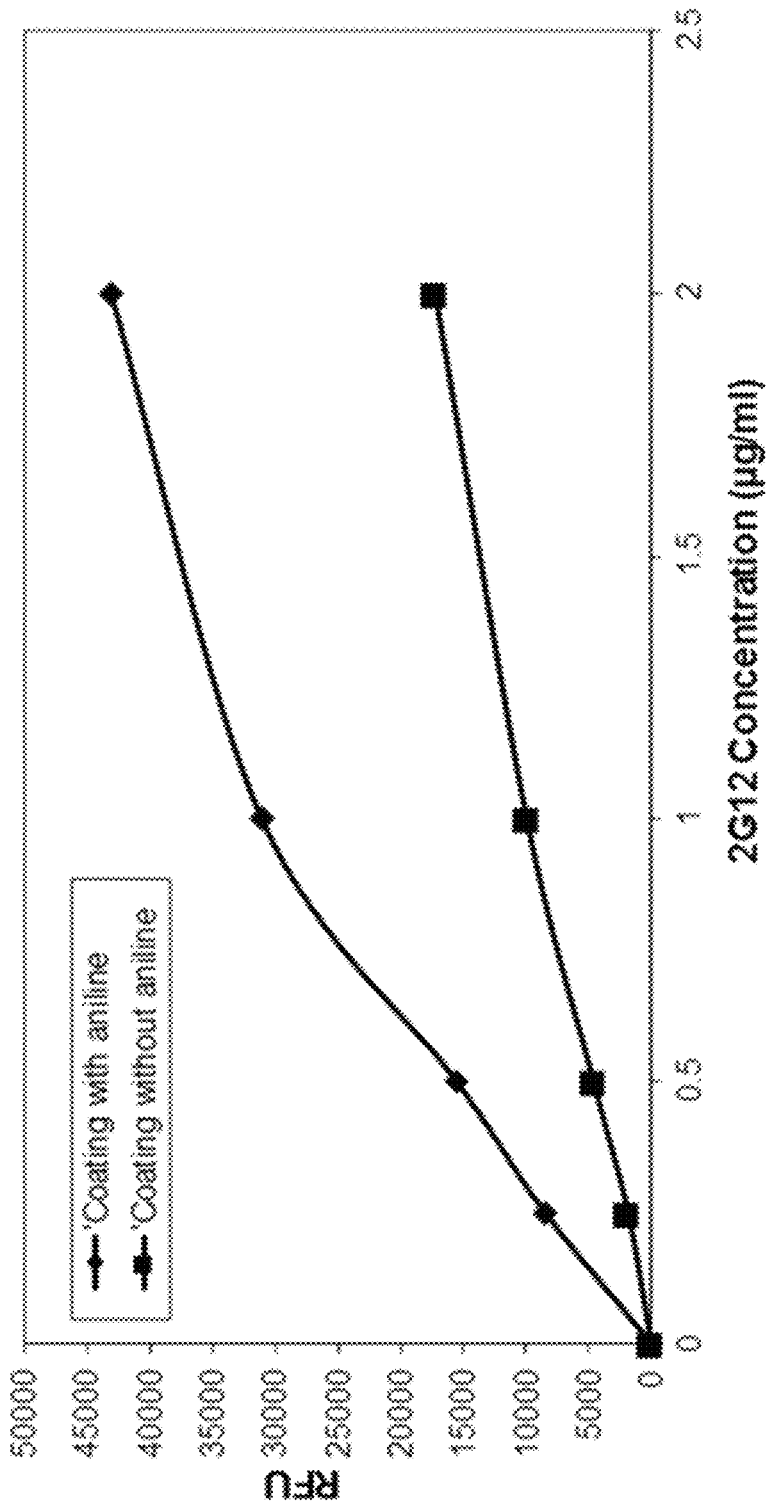
FIG. 10B illustrates a 2G12 antibody dynamic curve for binding to a high-mannose N-glycan (Man-8) (100 µM). 2G12 is pre-complexed with Cy3 labeled anti-Human IgG (1:4 ratio).
Figure 10C:
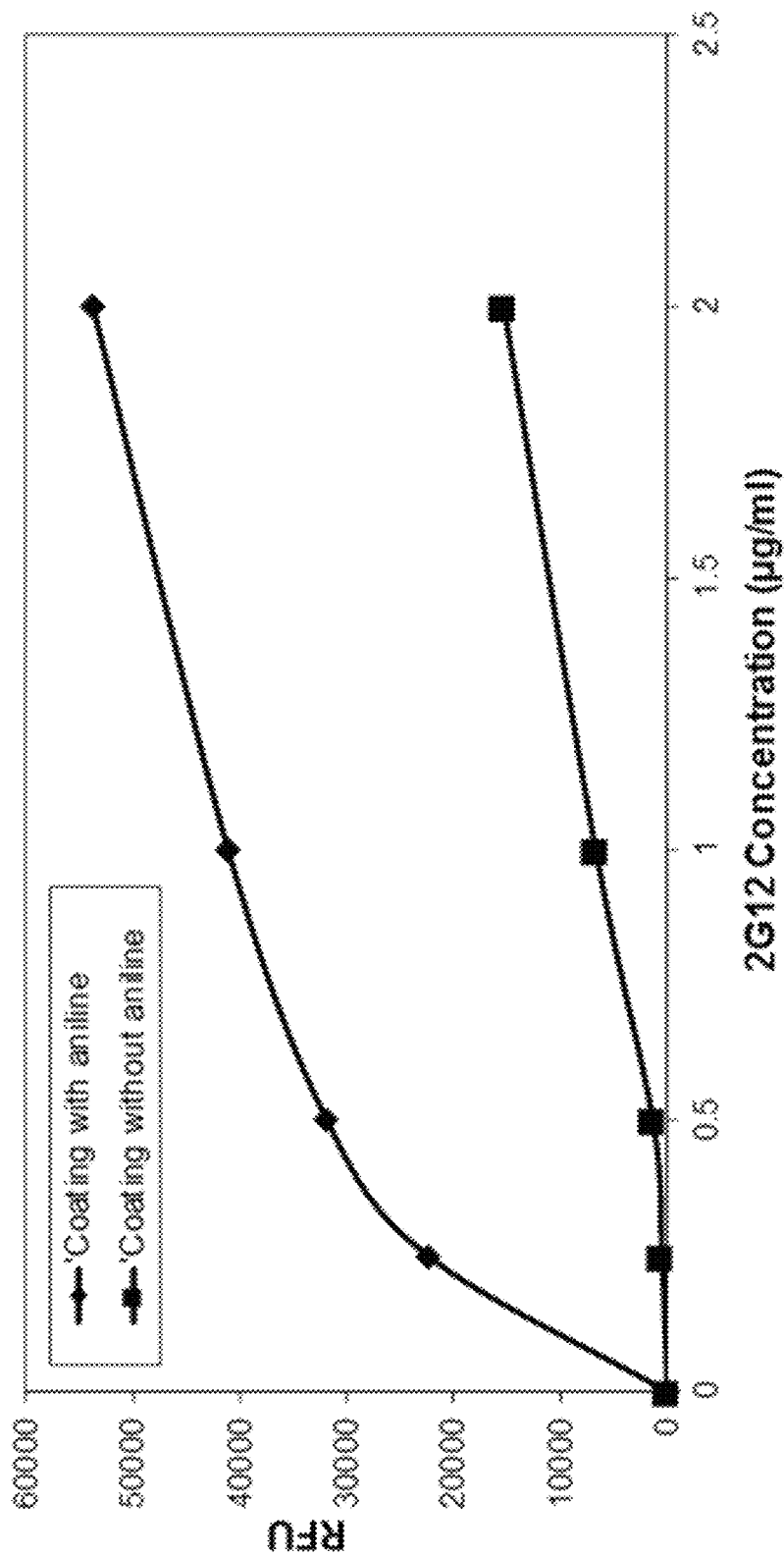
FIG. 10C shows a 2G12 antibody dynamic curve for binding to a high-mannose N-glycan (Man-9) (100 µM). 2G12 is pre-complexed with Cy3 labeled anti-Human IgG (1:4 ratio).
Figure 10D:
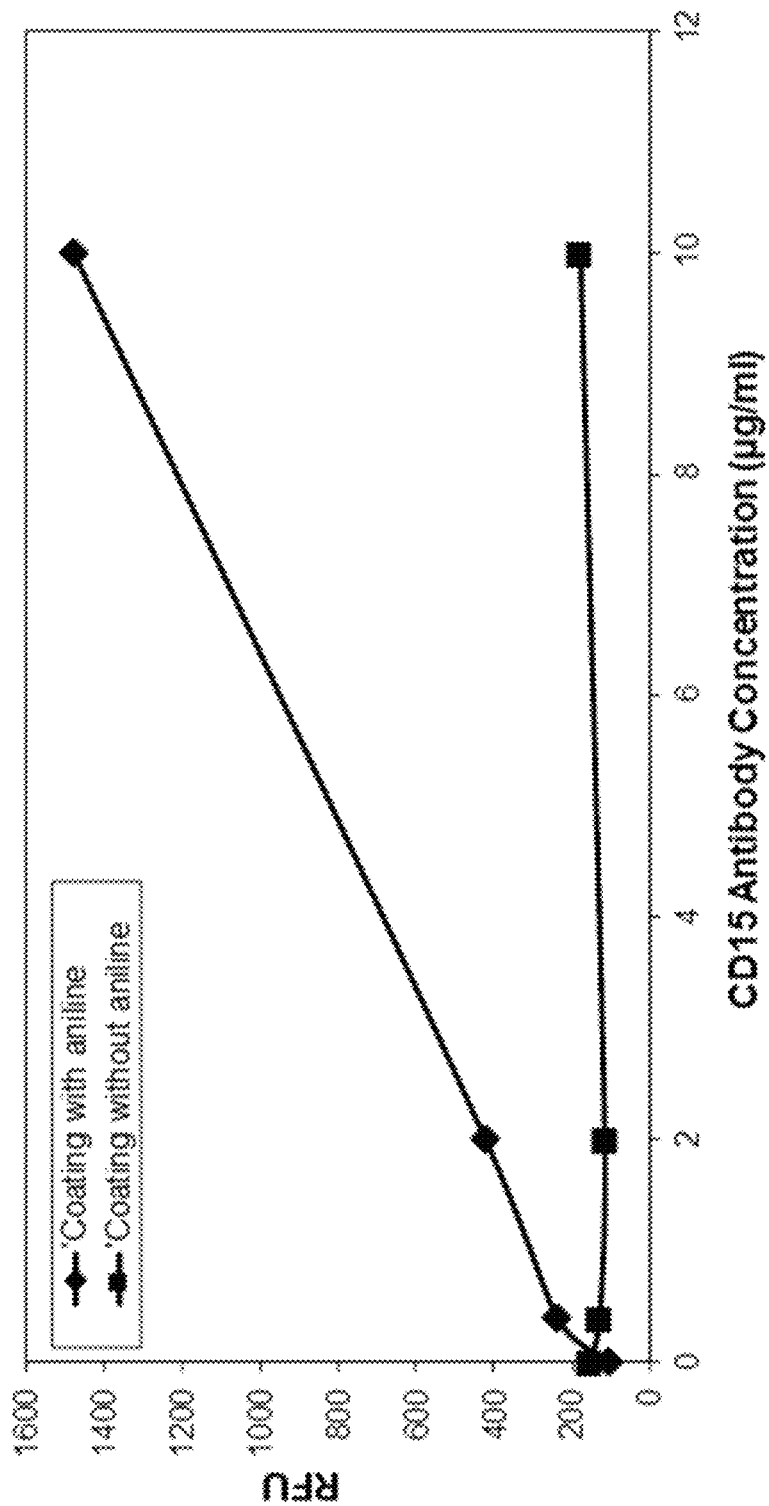
FIG. 10D shows CD15 (Lewis X) antibody dynamic curve for binding to a complex N-glycan (100 µM). CD15 antibody is detected with Alexa Fluor 555-labeled anti-mouse IgM secondary antibody.

On the aniline-coated substrate, all of the N-glycans containing L-fucose epitope(s) showed as expected specific binding to the AAL lectin (FIG. 10A). The HIV broadly neutralizing antibody 2G12 showed as expected specific binding to Man-8 and Man-9 N-glycans containing Manα1-2Manα1-2Mana epitope (FIG. 10B and FIG. 10C). The CD15 (Lewis X) antibody showed as expected specific binding to the glycan #29 containing Galβ1-4(Fucα1-3)GlcNAcβ (Lewis X antigen) epitope (FIG. 10D).

Example 10

Figure 12A:
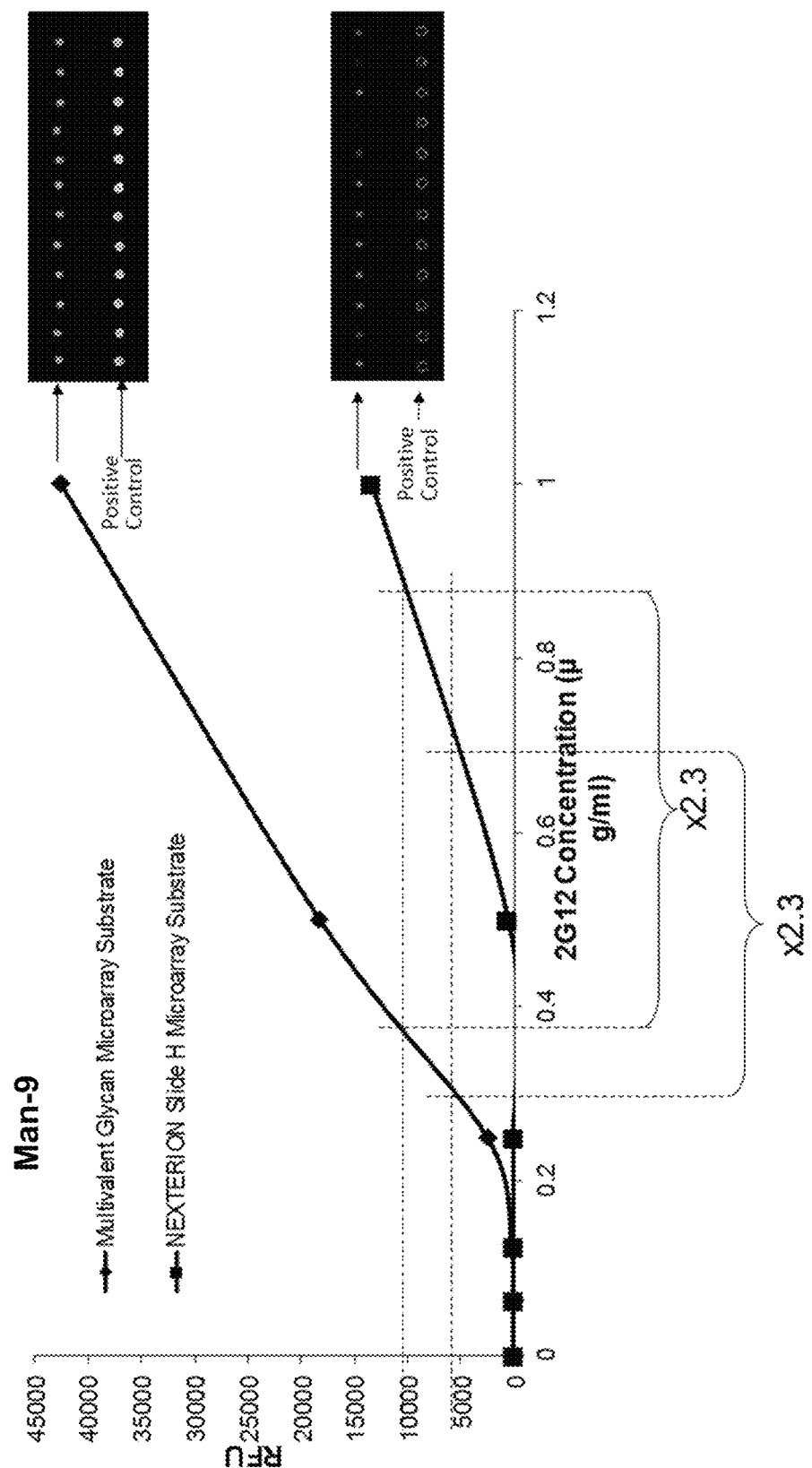
FIG. 12A shows the dynamic range of a 2G12 IgG antibody binding to a high-mannose N-glycan (Man-9). The microarray image for one antibody concentration (1 µg/ml) is illustrated on right.
Figure 12B:
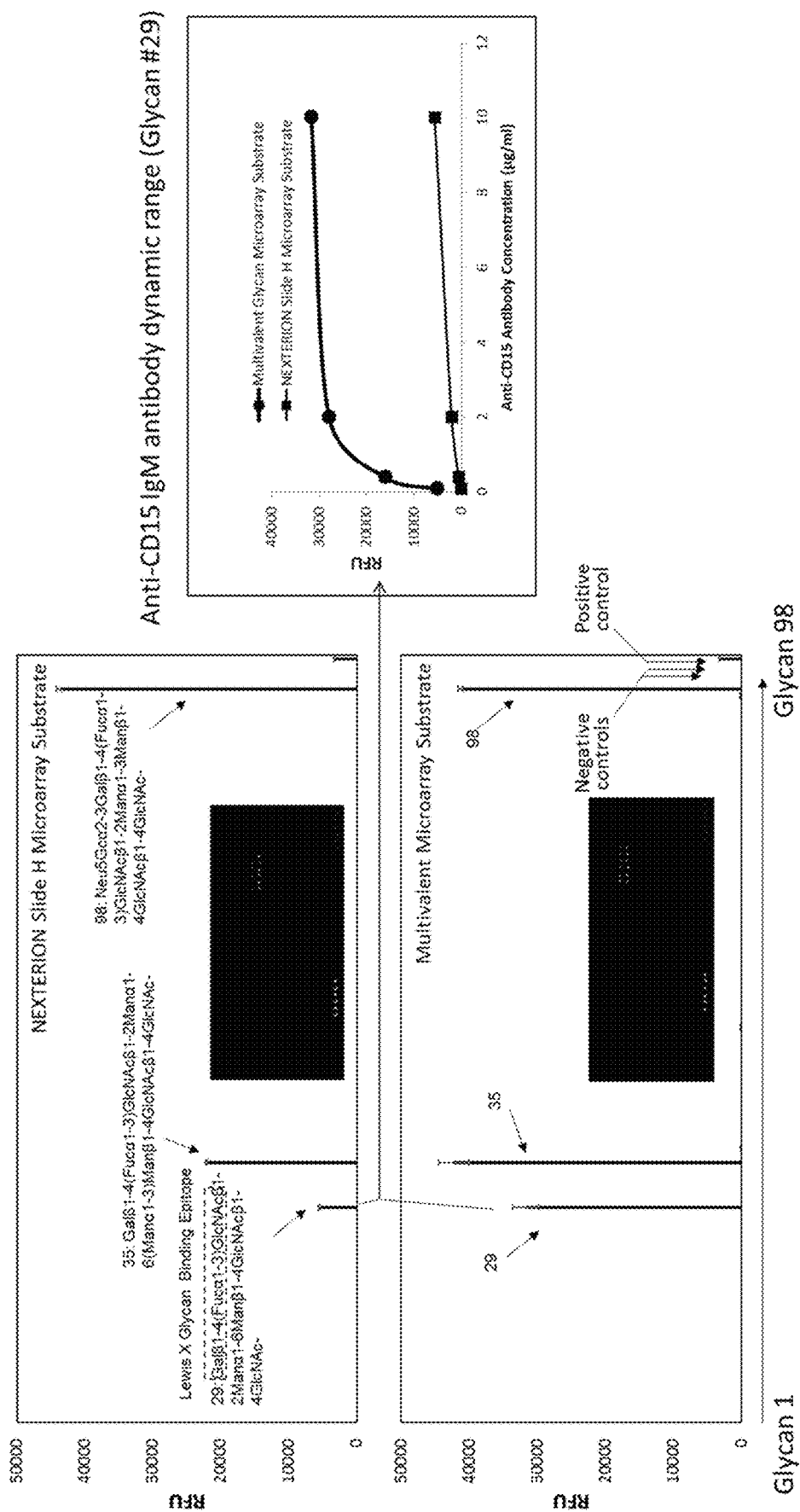
FIG. 12B shows interaction of an anti-glycan IgM antibody (anti-CD15 or Lewis X antibody) with 98 glycans printed on a non-multivalent NEXTERION Slide H microarray substrate and a multivalent glycan microarray substrate. The microarray image for one antibody concentration (10 µg/ml) is illustrated and inserted in the binding charts. The dynamic range curve for one antibody-glycan (Glycan 29, in Table 4, example 9) binding is plotted on the right.
Figure 12C:
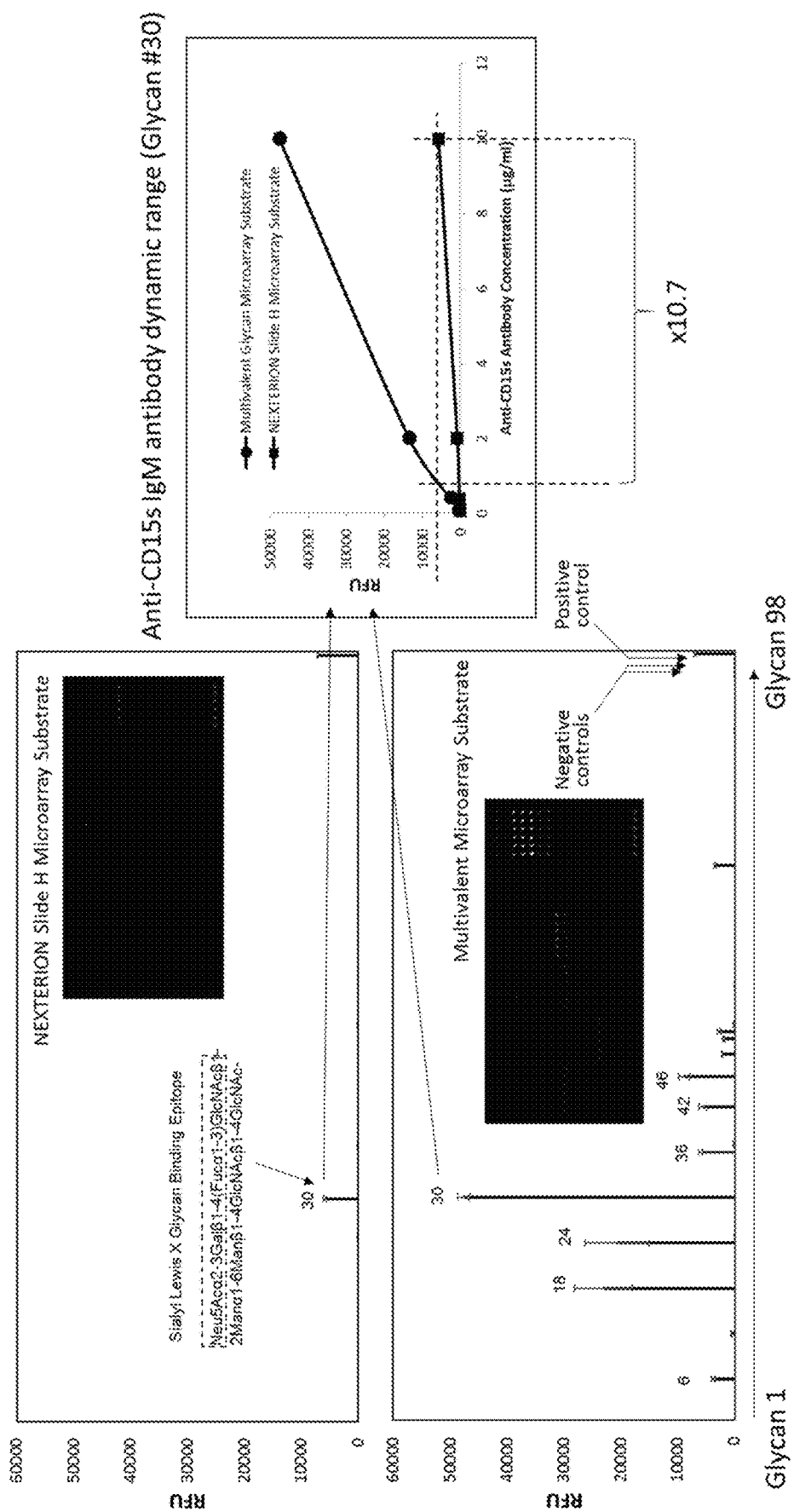
FIG. 12C shows interaction of an anti-glycan antibody (anti-CD15s or Sialyl Lewis X antibody) with glycans printed on a non-multivalent NEXTERION Slide H microarray substrate and a multivalent glycan microarray substrate. The microarray image for one antibody concentration (10 µg/ml) is illustrated and inserted in the binding charts. The dynamic range curve for one antibody-glycan (Glycan #30, in Table 4, example 9) binding is plotted on the right.
Figure 12D:
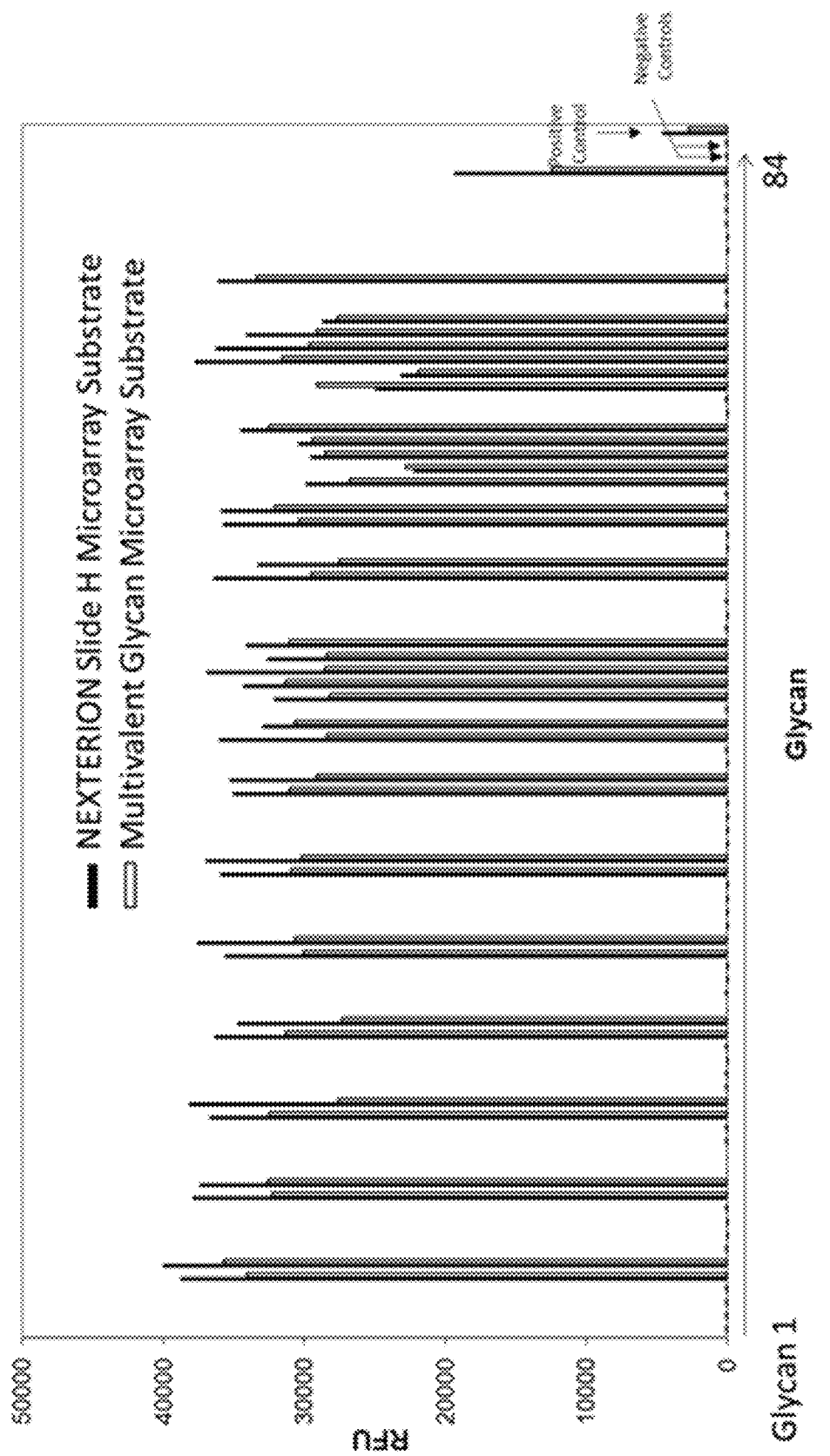
FIG. 12D shows detection of non-antibody glycan-binding protein (*Aleuria aurantia* Lectin, AAL) on NEXTERION Slide H microarray substrate (solid bars) and multivalent glycan microarray substrate (open bars).

Comparison of the multivalent glycan substrate of the present invention to prior art NEXTERION Slide H microarray substrate. FIG. 12A shows the dynamic range of a 2G12 IgG antibody binding to a high-mannose N-glycan (Man-9). The Multivalent Glycan Microarray Substrate is ~2.3 time more sensitive than the NEXTERION Slide H Microarray Substrate. The microarray image for one antibody concentration (1 μg/ml) is illustrated on right. FIG. 12B shows the interaction of an anti-glycan IgM antibody (anti-CD15 or Lewis X antibody) with 98 glycans (glycans listed in Table 4 in Example 9) printed on a non-multivalent NEXTERION Slide H microarray substrate and a multivalent glycan microarray substrate. The microarray image for one antibody concentration (10 μg/ml) is illustrated and inserted in the binding charts. The dynamic range curve for one antibody-glycan binding is plotted on the right. The multivalent glycan microarray substrates showed much higher binding affinity than the NEXTERION Slide H microarray substrate. FIG. 12C shows interaction of an anti-glycan antibody (anti-CD15s or Sialyl Lewis X antibody) with glycans printed on a non-multivalent NEXTERION Slide H microarray substrate and a multivalent glycan microarray substrate. The microarray image for one antibody concentration (10 μg/ml) is illustrated and inserted in the binding charts. The dynamic range curve for one antibody-glycan binding is plotted on the right. The anti-CD15s IgM antibody shows ~10.7 time more sensitivity on the Multivalent Glycan Microarray Substrate than the NEXTERION Slide H Microarray Substrate. FIG. 12D shows detection of non-antibody glycan-binding protein (*Aleuria aurantia* Lectin, AAL) on NEXTERION Slide H microarray substrate and multivalent glycan microarray substrate. The multivalent glycan microarray substrates showed similar binding affinity to the NEXTERION Slide H microarray substrate (solid bar vs. open bar in FIG. 12D).

Example 11

Figure 13B:
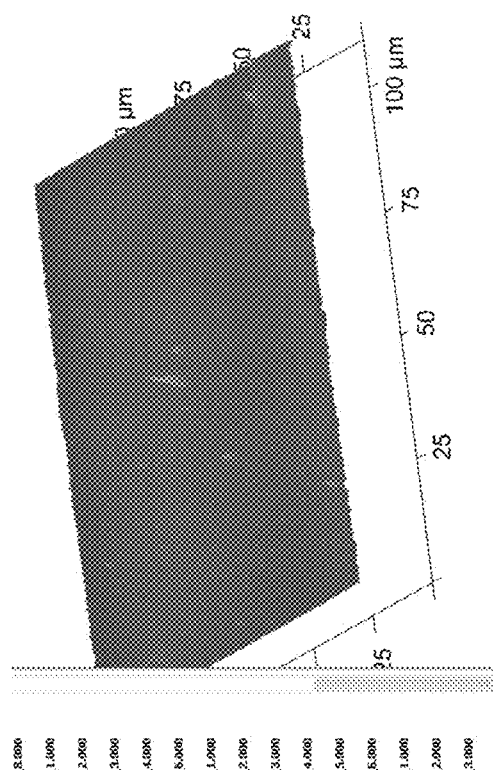
FIG. 13A, 13B, 13C, 13D illustrates AFM images (3D height) from scanning a 0.1 $mm^2$ area on surface of a hydrazide-functionalized multivalent substrate. The coating is wetted with water for 0 (dry) (FIG. 13A), 10 minutes (FIG. 13B), 20 minutes (FIG. 13C) and 30 minutes (FIG. 13D). The coating thickness increased with increasing times of incubation with water.
Figure 13A:
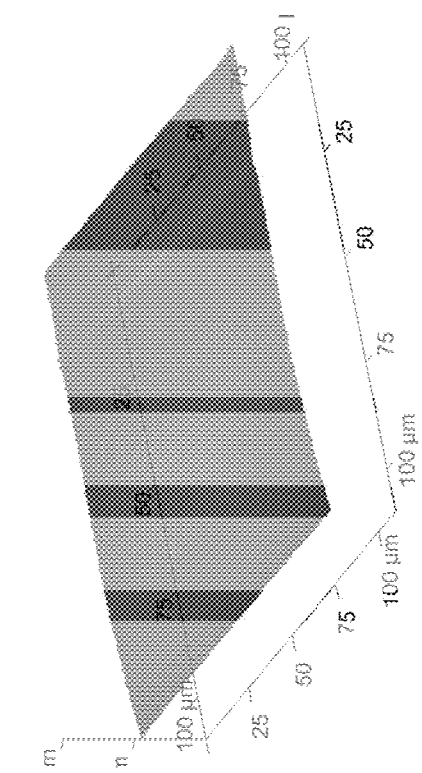
Figure 13D:
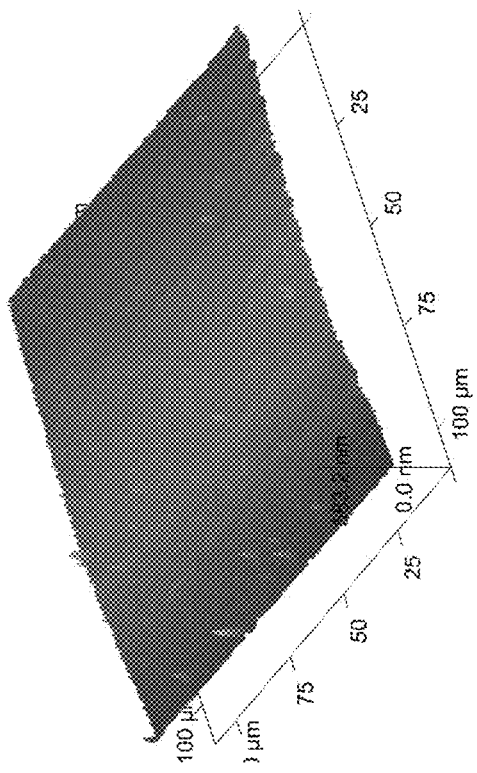
Figure 13C:
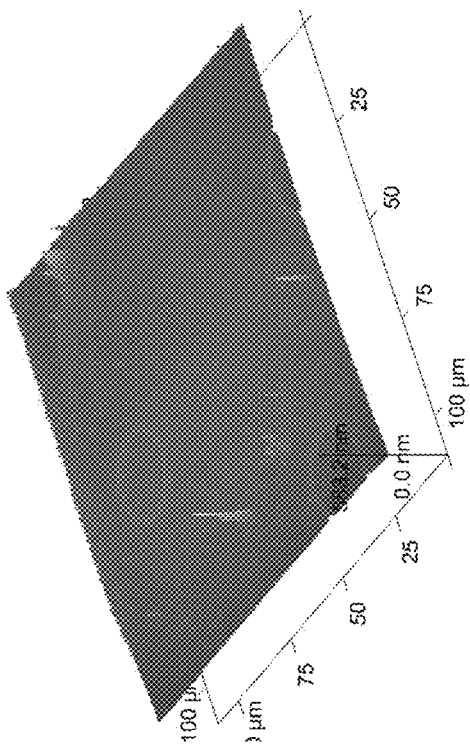

Comparison of the multivalent glycan substrate of the present invention to prior art illustrates an atomic force microscopy (AFM) image (3D height) from scanning a 0.1 mm² area on surface of a hydrazide-functionalized multivalent substrate. See FIGS. 13A-13D. The coating is wetted with water for 0 (FIG. 13A), 10 (FIG. 13B), 20 (FIG. 13C) and 30 (FIG. 13D) minutes, respectively. The coating thickness was getting larger along with time of wetting coating under water. Table 5 shows the coating thickness of a hydrazide-functionalized multivalent substrate. AFM is used for exam of the coating thickness and roughness. For NHS-functionalized multivalent substrate in dry condition, the average coating thickness is 17 nm, the average peak-to-trough roughness is 10 nm, and the average RMS roughness is 12 nm. For hydrazide-functionalized multivalent substrate in dry condition, the average coating thickness is 57 nm, the average peak-to-trough roughness is 8 nm, and the average RMS roughness is 11 nm. The coatings of the multivalent substrates can get expanded during water wetting (Table 5). The coating expansion is mainly caused by expansion of coating matrix in the second coating solution. The coating expansion can form porous structure on the surface during the latter binding assay in aqueous buffers on the microarray substrates. This porous structure can prevent trapping of unbound target on the surface, which results in unbound targets being easily washed off, leading to ultralow background on microarray substrate surface.

TABLE 5

| Condition | Coating Thickness (nm) |
|---|---|
| Dry | 56.5 |
| 10 min under water | 60.1 |
| 20 min under water | 75.9 |
| 30 min under water | 90.7 |

The terms and expressions which have been employed herein are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments, exemplary embodiments

STATEMENTS REGARDING INCORPORATION BY REFERENCE AND VARIATIONS

All references throughout this application, for example patent documents including issued or granted patents or equivalents; patent application publications; and non-patent literature documents or other source material; are hereby incorporated by reference herein in their entireties, as though individually incorporated by reference, to the extent each reference is at least partially not inconsistent with the disclosure in this application (for example, a reference that is partially inconsistent is incorporated by reference except for the partially inconsistent portion of the reference).

The terms and expressions which have been employed herein are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments, exemplary embodiments and optional features, modification and variation of the concepts herein disclosed may be resorted to by those skilled in the art, and that such modifications and variations are considered to be within the scope of this invention as defined by the appended claims. The specific embodiments provided herein are examples of useful embodiments of the present invention and it will be apparent to one skilled in the art that the present invention may be carried out using a large number of variations of the devices, device components, methods steps set forth in the present description. As will be obvious to one of skill in the art, methods and devices useful for the present methods can include a large number of optional composition and processing elements and steps.

Whenever a range is given in the specification, for example, a temperature range, a time range, or a composition or concentration range, all intermediate ranges and subranges, as well as all individual values included in the ranges given are intended to be included in the disclosure. It will be understood that any subranges or individual values in a range or subrange that are included in the description herein can be excluded from the claims herein.

All patents and publications mentioned in the specification are indicative of the levels of skill of those skilled in the art to which the invention pertains. References cited herein are incorporated by reference herein in their entirety to indicate the state of the art as of their publication or filing date and it is intended that this information can be employed herein, if needed, to exclude specific embodiments that are in the prior art. For example, when composition of matter are claimed, it should be understood that compounds known and available in the art prior to Applicant's invention, including compounds for which an enabling disclosure is provided in the references cited herein, are not intended to be included in the composition of matter claims herein.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. In each instance herein any of the terms "comprising", "consisting essentially of" and "consisting of" may be replaced with either of the other two terms. The invention illustratively described herein suitably may be practiced in the absence of any element or elements, limitation or limitations which is not specifically disclosed herein.

One of ordinary skill in the art will appreciate that starting materials, biological materials, reagents, synthetic methods, purification methods, analytical methods, assay methods, and biological methods other than those specifically exemplified can be employed in the practice of the invention without resort to undue experimentation. All art-known functional equivalents, of any such materials and methods are intended to be included in this invention. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

I claim:

1. A multivalent glycan microarray, comprising:
a solid substrate;
one or more branched polymers bonded to the solid substrate via one or more non-self-crosslinking silane-based linker reagents;
one or more succinimidyl homo-bifunctional linkers selected from the group consisting of N,N'-disuccinimidyl carbonate (DSC), N,N'-disuccinimidyl tartrate (DST), N,N'-disuccinimidyl oxalate (DSO), N,N'-disuccinimidyl glutarate (DSG), N,N'-disuccinimidyl suberate (DSS), N,N'-disuccinimidyl homobifunctional poly(ethylene glycol) (PEG), and combinations thereof, wherein at least one functional group of the succinimidyl homo-bifunctional linker is bonded to said branched polymers; and
a plurality of one or more glycans, wherein the plurality of glycans is bonded to said bifunctional linker through the other said functional group to form the multivalent glycan microarray.

2. The multivalent glycan microarray of claim 1, wherein the multivalent glycan microarray binds to one or more glycan-binding proteins selected from the group consisting of a lectin, a lectin-like cellular receptor, an antibody, fused proteins, native proteins, recombinant proteins, or any combination thereof.

3. The multivalent glycan microarray of claim 2, wherein the glycan-binding protein is an antibody and is selected from the group consisting of anti-STn antibodies (B72.3, STn 219, CC49), anti-Neu5Gc antibody, CD15 (SSEA-1) antibody (anti-Lewis X antibody), CD15s antibody (anti-sialyl lewis X antibody), anti-Tn antibody (Tn 218), anti-MUC1 antibody, HIV broadly neutralizing antibodies, anti-Gb3 antibody (CD77 antibody), anti-GD3 antibody, anti-fucosyl-GM1 antibody (BMS-986012), anti-GM3 antibody, anti-Lewis A antibody, anti-sialyl lewis A antibody, anti-Globo-H antibody, anti-GD2 antibody, and anti-NGcGM3 antibody.

4. The multivalent glycan microarray of claim 1, wherein the microarray further comprises a blocking reagent comprising either a poly(ethylene glycol) (PEG) or a PEG nonionic surfactant attached to the solid surface through one or more self-crosslinking silane-based linker reagents, and wherein the blocking reagent is selected from the group consisting of a PEG polymer, poly(ethylene glycol) sorbitol hexaoleate, poly(ethylene glycol) sorbitan tetraoleate, and combinations thereof.

5. The multivalent glycan microarray of claim 2, wherein the microarray further comprises a blocking reagent comprising either a poly(ethylene glycol) (PEG) or a PEG nonionic surfactant attached to the solid surface through one or more self-crosslinking silane-based linker reagents.

6. The multivalent glycan microarray of claim 1, wherein said branched polymer comprises a multi-arm polyethylene glycol (PEG) polymer which comprises a number of valency sites in the range from 2, for Y-shaped PEG, to 8, for 8-armed PEG; or wherein said branched polymer comprises a highly branched polyethylenimine (PEI) polymer which comprises a number of valency sites in the range 10, for a 800 Da low-molecular-weight PEI, to 211, for a 25,000 Da high-molecular-weight PEI.

7. A method for making a functionalized substrate for a multivalent glycan microarray, comprising:
providing a solid substrate having a contact surface,
contacting at least a portion of said contact surface of said solid substrate with an active coating mixture comprising one or more non-self-crosslinking silane-based linker reagents; one or more branched polymers; and one or more succinimidyl homo-bifunctional linkers selected from the group consisting of N,N'-disuccinimidyl carbonate (DSC), N,N'-disuccinimidyl tartrate (DST), N,N'-disuccinimidyl oxalate (DSO), N,N'-disuccinimidyl glutarate (DSG), N,N'-disuccinimidyl suberate (DSS), N,N'-disuccinimidyl homobifunctional poly(ethylene glycol) (PEG), and combinations thereof to create a functionalized substrate; and
curing said functionalized substrate, wherein said functionalized substrate comprises a plurality of functional groups for binding glycans to form said multivalent glycan microarray.

8. The method of claim 7, further comprising:
contacting said functionalized substrate with at least one glycan under conditions to allow bonding of said glycan to said functional groups to form a multivalent glycan microarray.

9. The method of claim 7, wherein the method further comprises contacting at least a portion of said contact surface of said solid substrate with a blocking mixture to reduce nonspecific binding of glycan-binding proteins to the solid substrate.

10. The method of claim 9, wherein said blocking mixture comprises a self-crosslinking silane-based linker reagent, and a blocking reagent comprising poly(ethylene glycol) (PEG) or a PEG nonionic surfactant, and wherein the blocking reagent is selected from the group consisting of a PEG polymer, poly(ethylene glycol) sorbitol hexaoleate, poly(ethylene glycol) sorbitan tetraoleate, and combinations thereof.

11. The method of claim 8, wherein the method further comprises contacting at least a portion of said contact surface of said solid substrate with a blocking mixture to reduce nonspecific binding of glycan-binding proteins to the solid substrate.

12. The method of claim 10, wherein said self-crosslinking silane-based reagent is an azido functionalized trialkoxysilane selected from the group consisting of 3-azidopropyltriethoxysilane, p-azidomethylphenyltrimethoxysilane, 6-azidosulfonylhexyltriethoxysilane, 4-(azidosulfonyl)phenethyltrimethoxysilane, (azidomethyl)phenethyltrimethoxysilane, and combinations thereof.

13. The method of claim 7, wherein the branched polymer is selected from the group consisting of a branched polymer comprises a polyamidoamine (PAMAM) dendrimer, a multi-arm polyethylene glycol (PEG), a highly branched polyethylenimine (PEI) polymer, a PEG-core dendrimer, a multi-arm polyethylene glycol (PEG) polymer, a poly(acrylate), a polyamine, a polyamide, a polyether, a polyester, a poly(methyl acrylate), a polyphenylenes, and a polystyrene.

14. The method of claim 13, wherein said branched polymer comprises a terminal group selected from the group consisting of a sodium carboxylate terminal group, a hydroxyl terminal group, a primary amine terminal group, an amidoethanol terminal group, a succinamic acid terminal group, a succinimidyl terminal group, and a mixture of primary and secondary amine terminal group.

15. The method of claim 9, wherein said active coating mixture and blocking mixture are applied simultaneously to the substrate in a ratio of between 10:1 and 1:20.

16. The method of claim 7, wherein said non self-crosslinking silane-based linker reagent is a functionalized alkoxysilane.

17. The method of claim 7, wherein said contacting comprises spin-coating, vapor-coating, dip-coating, spray-coating, or combinations thereof.

18. The method of claim 7, wherein said curing step comprises a thermal curing process in a vacuum oven or UV curing process in a UV crosslinker.

19. The method of claim 18, wherein the curing step is a thermal curing process with a curing temperature between 70° C. and 150° C., a curing duration between 1 and 4 hours, and a curing pressure of less than atmospheric pressure.

20. A method for identification of interactions between a multivalent glycan microarray and a glycan-binding protein, comprising:
providing a sample containing at least one glycan-binding protein;
providing a multivalent glycan microarray according to claim 1;
contacting the sample and the multivalent glycan microarray; and
detecting an interaction between the glycans in the multivalent glycan microarray and said glycan-binding protein.

* * * * *